(12) United States Patent
Takeuchi et al.

(10) Patent No.: US 12,115,161 B2
(45) Date of Patent: Oct. 15, 2024

(54) PROPHYLACTIC AND/OR THERAPEUTIC AGENT FOR INFLAMMATORY DISEASES WHICH CONTAINS PYRROLOPYRIMIDINE COMPOUND AS ACTIVE INGREDIENT

(71) Applicant: KEIO UNIVERSITY, Tokyo (JP)

(72) Inventors: Tsutomu Takeuchi, Tokyo (JP); Katsuya Suzuki, Tokyo (JP); Keiko Yoshimoto, Tokyo (JP)

(73) Assignee: Keio University, Tokyo (JP)

( * ) Notice: Subject to any disclaimer, the term of this patent is extended or adjusted under 35 U.S.C. 154(b) by 1008 days.

(21) Appl. No.: 17/054,448

(22) PCT Filed: May 10, 2019

(86) PCT No.: PCT/JP2019/018710
§ 371 (c)(1),
(2) Date: Jul. 7, 2021

(87) PCT Pub. No.: WO2019/216409
PCT Pub. Date: Nov. 14, 2019

(65) Prior Publication Data
US 2021/0393634 A1  Dec. 23, 2021

(30) Foreign Application Priority Data
May 11, 2018  (JP) .................. 2018-092068

(51) Int. Cl.
*A61K 31/519* (2006.01)
*A61P 37/06* (2006.01)

(52) U.S. Cl.
CPC ............ *A61K 31/519* (2013.01); *A61P 37/06* (2018.01)

(58) Field of Classification Search
CPC ............... A61K 31/519; A61P 37/06
See application file for complete search history.

(56) References Cited

U.S. PATENT DOCUMENTS

2017/0034245 A1 * 2/2017 Chough et al. ...... C07D 487/04
2018/0237440 A1   8/2018 Chough et al.

FOREIGN PATENT DOCUMENTS

| JP | 2012116777 A | 6/2012 |
| WO | 2015053270 A1 | 4/2015 |
| WO | 2017034245 A1 | 3/2017 |

OTHER PUBLICATIONS

Yoshimoto et al. "Regulatory Mechanisms for the Production of BAFF and IL-6 are Impaired in Monocytes of Patients of Primary Sjogren's Syndrome," Arthritis Research & Therapy 2011, 13:R170.
International Search Report dated Jun. 25, 2019 for related Application No. PCT/JP2019/018710.

* cited by examiner

*Primary Examiner* — Erich A Leeser
(74) *Attorney, Agent, or Firm* — HSML P.C.

(57) ABSTRACT

The present invention provides a prophylactic and/or therapeutic agent for inflammatory disease including a compound or a salt thereof, or a solvate thereof, the compound represented by a formula (1):

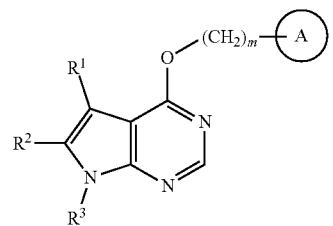

[where each sign is defined as described in the description] as an active ingredient.

13 Claims, 4 Drawing Sheets

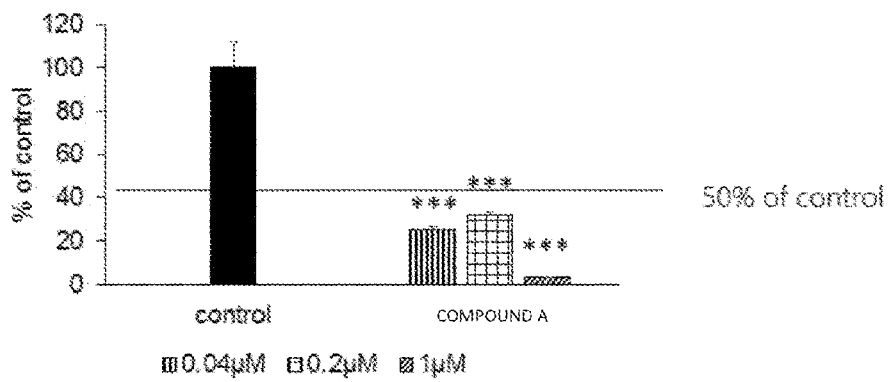
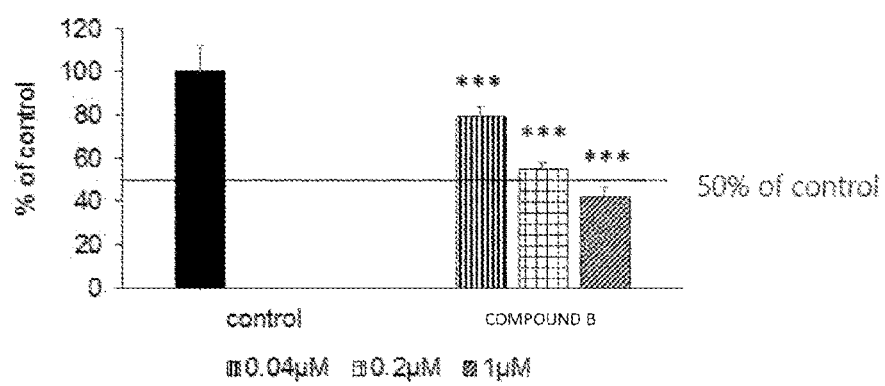
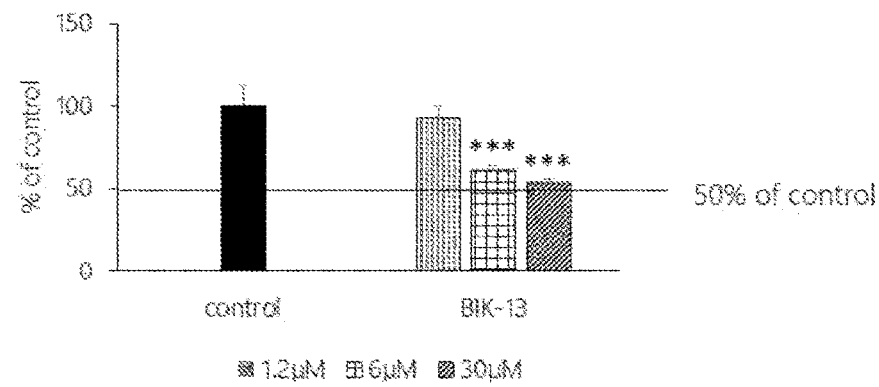

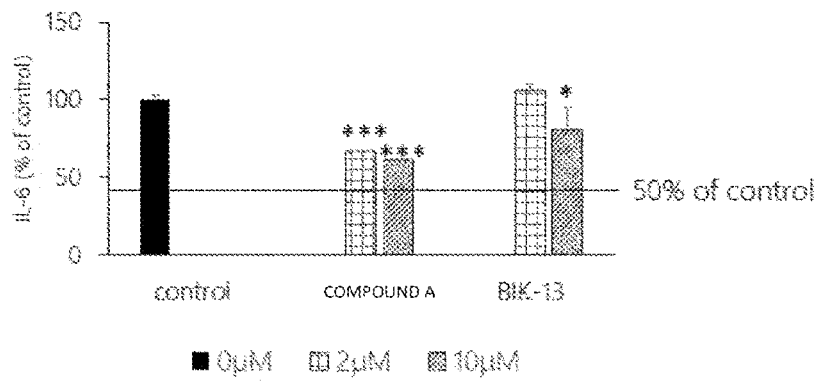
[FIG.2]
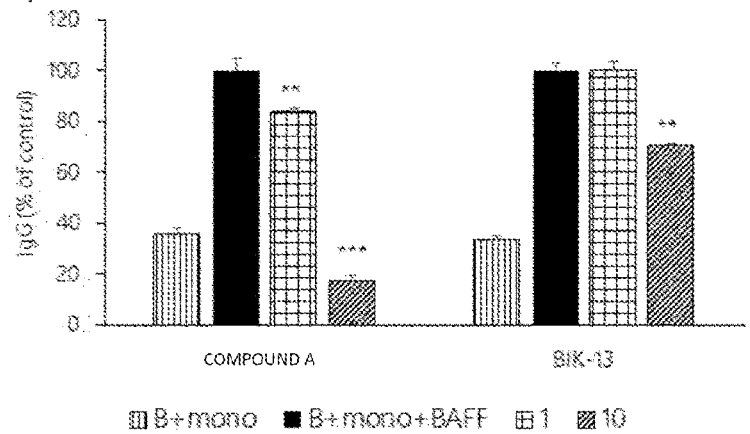
[FIG.3]
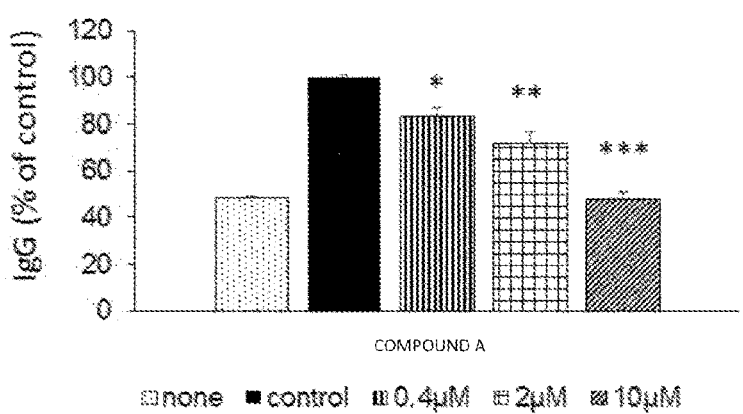
[FIG.4]

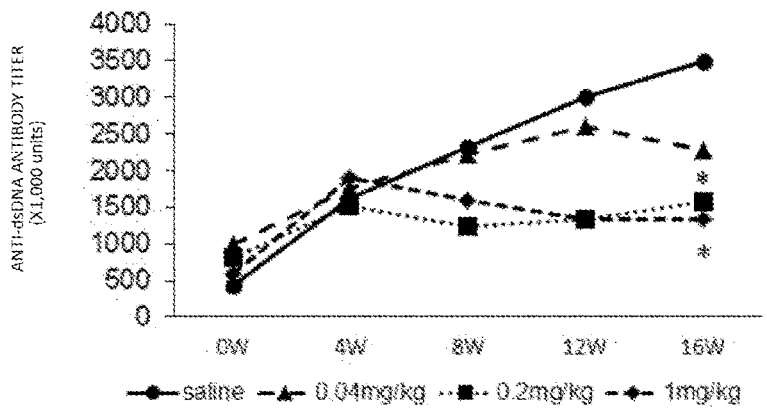
[FIG.5]
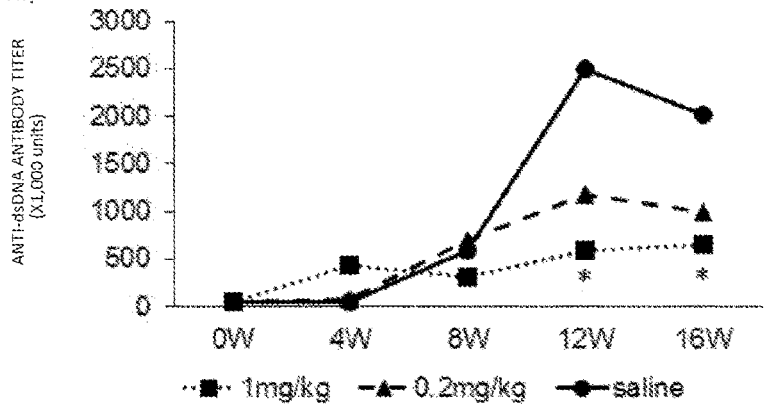
[FIG.6]
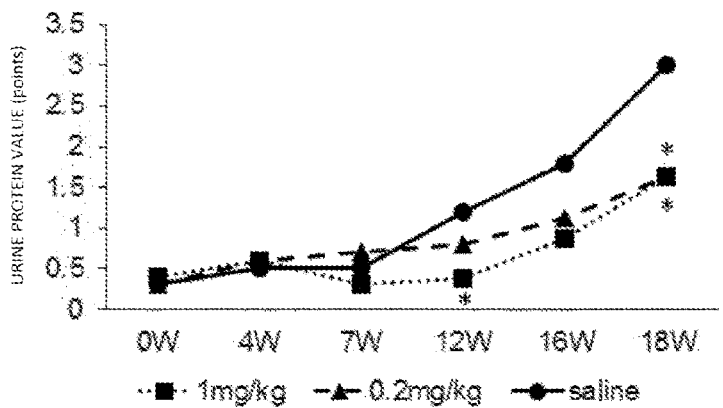
[FIG.7]

[FIG.8A]
[FIG.8B]
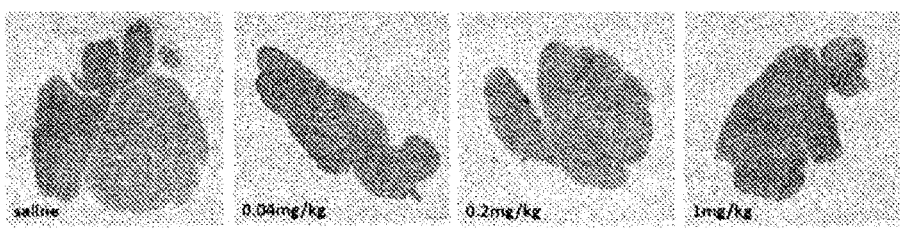
[FIG.8C]
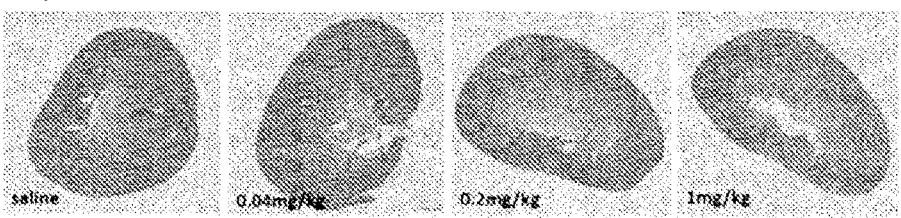

PROPHYLACTIC AND/OR THERAPEUTIC AGENT FOR INFLAMMATORY DISEASES WHICH CONTAINS PYRROLOPYRIMIDINE COMPOUND AS ACTIVE INGREDIENT

TECHNICAL FIELD

The present invention relates to a pharmaceutical for preventing and treating inflammatory diseases, such as Sjögren syndrome, containing a pyrrolopyrimidine compound as an active ingredient. The present invention relates more specifically to a prophylactic and/or therapeutic agent for inflammatory diseases, such as Sjögren syndrome, containing a pyrrolopyrimidine compound as an active ingredient, the pyrrolopyrimidine compound inhibiting an IL-6 production enhancing effect of a BAFF (B cell activating factor belonging to TNF superfamily).

BACKGROUND ART

Sjögren syndrome (abbreviated as SS or SjS, hereinafter, may be referred to as "SS") is one of the intractable diseases designated in Japan and is an inflammatory disease with main symptoms of chronic sialadenitis and keratoconjunctivitis sicca. SS also produces various autoantibodies (anti-SS-A antibody, anti-SS-B antibody, antinuclear antibody, rheumatoid factor, etc.) and develops hypergammaglobulinemia, and is an organ specific autoimmune disease targeting lacrimal glands and salivary glands as well as a systemic autoimmune disease with systemic organ lesions. Representative examples of the organ specific symptoms include dryness of the eyes (dryeyes), dryness of the mouth, dryness of the nasal cavity, swelling and pain in the salivary glands, and the like. Particularly frequent examples of the systemic symptoms are fatigue, decline in memory, and headache, and other examples include vertigo, decline in attention, inconsistent mood, depressive tendencies, and the like.

SS can be classified into secondary Sjögren syndrome associated with collagen diseases (rheumatoid arthritis, systemic lupus erythematosus, scleroderma, dermatomyositis, mixed connective tissue disease) and primary Sjögren syndrome (pSS) not associated with them. Moreover, pSS can be classified into glandular manifestations with lesions localized in the lacrimal and salivary glands and extraglandular manifestations with lesions throughout various systemic organs.

SS is diagnosed by satisfying two of the following four categories based on the diagnosis criteria revised in 1999 by the Ministry of Health, Labour and Welfare of Japan.

1. Defined Positive on any One of the Following Histopathological Biopsies:
   A) lymphocytic infiltration with a focus score of 1 or more per 4 mm² in labial gland tissues;
   B) lymphocytic infiltration with a focus score of 1 or more per 4 mm² in lacrimal gland tissues.

2. Defined Positive on any One of the Following Oral Examinations:
   A) abnormalities in stage I (punctate shadows with a diameter of 1 mm or less) or higher in sialography;
   B) reduced salivation (10 mL or less for ten minutes in chewing gum test or 2 g or less for two minutes in Saxon test) and hypofunction in salivary gland scintigraphy.

3. Defined Positive on any One of the Following Ophthalmologic Examinations:
   A) 5 mm/5 min or less by Schirmer test and positive in rose bengal test;
   B) 5 mm/5 min or less by Schirmer test and positive in fluorescent (fluorescein) staining test.

4. Defined Positive on any One of the Following Serological Examinations:
   A) positive for anti-SS-A antibody;
   B) positive for anti-SS-B antibody.

SS often occurs in middle-aged women and the age group of the patients with a peak at fifties while the reported incidence varies from children to elderly people in their eighties. The ratio of men to women is 1:14 and there are more female patients. According to data by a study group of by the Ministry of Health, Labour and Welfare of Japan, the number of patients is assumed to be approximately 66,300. However, including potential patients that have not been treated in health care facilities, the number of SS patients in Japan is estimated to reach between 100 and 300 thousand.

Treatment of SS is supposedly highly needed because there are a large number of patients and the QoL is severely impaired by worsening of symptoms, such as dryness of the eyes and the mouth. However, the cause of autoimmune response is currently not clear and a method of radically curing SS has not yet found. Goals of clinical treatment are thus relief of the sicca symptoms and suppression of activity of the disease to prevent the development.

BAFF (abbreviation of a B-cell-activating factor of the TNF family and may be referred to as BLyS, TALL-1, THANK, zTNF4, TNFSF13B, or a Kay ligand) is a kind of cytokine discovered as a survival and maturation factor for B cells. BAFF is regarded as a member of a superfamily of TNF-α, which is inflammatory cytokine. BAFF is mainly produced in monocytes and dendritic cells and is also known to be produced in T cells.

There are three kinds of transmembrane protein of BCMA (B cell maturation antigen, also known as TNFRSF17), TACI (Transmembrane activator and CAML-interactor, also known as TNFRSF13B), and BR3 (BLyS receptor-3, also known as BAFF-R, TNFRSF13C) reported as BAFF receptors, and these receptors are members of a TNF receptor superfamily, similar to the ligand.

It is considered that a c-terminal soluble fragment (sBAFF) of BAFF is secreted from the cell and bound to a BAFF receptor to induce signal transmission in various paths. BAFF is reported to, as a main action to B cells, lead to Bcl-2 antagonistic to apoptosis and lead to activation of B cells, including survival extension of B cells and enhancement of the production of IgM and IgG, which are immunoglobulin, for enhancement of autoantibody overproduction.

It is suggested that enhancement of cellular function induced by BAFF is related to autoimmune diseases because of a pSS-like morbid state developed in transgenic mice overexpressing BAFF in lymphoid cells, high concentrations of BAFF found in the serum of pSS patients and systemic lupus erythematosus (SLE) patients, and the like.

The present inventors found pyrrolopyrimidine compounds inhibiting the binding action between BAFF and BAFF receptor and reported that these compounds were useful as prophylactic and/or therapeutic agents for autoimmune diseases (rheumatoid arthritis, systemic lupus erythematosus, Sjögren syndrome, systemic sclerosis, multiple sclerosis, common variable immunodeficiency, etc.), acquired immunodeficiency syndrome, and non-Hodgkin lymphoma (precursor B cell lymphoblastic lymphoma, chronic B-lymphocytic leukemia, precursor cell leukemia, small lymphocytic lymphoma, lymphoplasmacytic lymphoma, immunocytoma, mantle cell lymphoma, follicular lymphoma, marginal zone lymphoma, hairy cell leukemia, plasmacytoma, plasma cell myeloma, diffuse large cell lymphoma, Burkitt lymphoma, etc.) (PTLs 1 and 2). However, the relationship between the structure and the function of the pyrrolopyrimidine compounds is not sufficiently clear and it is not yet clearly understood which structure of the compounds is prophylactically and/or therapeutically effective for the autoimmune diseases and the inflammatory diseases, including SS and SLE.

CITATION LIST

Patent Literature

PTL 1: JP 2012-116777 A
PTL 2: WO 2015/053270 A1

Non-Patent Literature

NPL 1: Yoshimoto K et al., Arthritis Res. Ther. (2011) 13: R170

SUMMARY OF INVENTION

Technical Problem

It is an object of the present invention to provide a pharmaceutical composition that contains a pyrrolopyrrolidine compound capable of inhibiting cell response induced by BAFF as an active ingredient and is prophylactically or therapeutically useful for autoimmune diseases and inflammatory diseases, such as Sjögren syndrome.

Solution to Problem

The present inventors had found that production control mechanisms for both cytokines of BAFF and IL-6 are impaired in monocytes of pSS patients (NPL 1). It is considered that IL-6 plays an important role in autoantibody production through promotion of B cell differentiation, resulting in the incidence of pSS. The present inventors focused their attention on monocyte response in the presence of BAFF stimuli and newly found pyrrolopyrrolidine compounds that had not been recognized to act on inflammatory diseases in the past by compound screening based on the effect of inhibiting the IL-6 production enhancement as an index. The present inventors newly found, as a representative compound, 2-[4-{(7-benzyl-5,6-dimethyl-7H-pyrrolo[2,3-d]pyrimidin-4-yl)oxy}piperidin-1-yl]-N(cyclopropylmethyl)acetamide. As another representative compound, 3-[4-{(7-cyclopentyl-5,6-dimethyl-7H-pyrrolo[2,3-d]pyrimidin-4-yl)oxy}piperidin-1-yl]propanenitrile was also found. The present inventors found that the pyrrolopyrimidine compounds also exhibit an effective inhibiting action on IgG production enhancement in BAFF stimulation. The present inventors have completed the present invention based on these findings.

The present invention more specifically relates to the following (1) through (72).

(1) A prophylactic and/or therapeutic agent for inflammatory disease, comprising: a compound or a salt thereof, or a solvate thereof, the compound represented by a formula (1) below:

[Chem. 1]

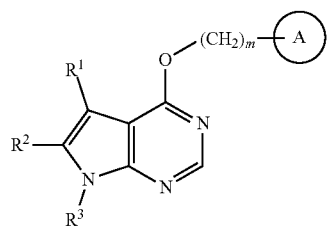

(1)

[where a ring A denotes a group represented by a formula (A) below

[Chem. 2]

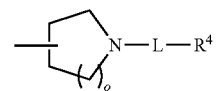

(A)

(where $R^4$ denotes a (($C_{3-6}$ cycloalkyl) ($C_{1-3}$ alkyl)) amino or nitrile group, L denotes a formula —$(CH_2)_n$—, —$CH_2C(O)$—, or —$C(O)CH_2$—, n denotes an integer from 0 to 3, and o denotes a natural number from 1 to 3),
$R^1$ and $R^2$, being same or different from each other, denote a hydrogen atom or a $C_{1-6}$ alkyl group, $R^3$ denotes a $C_{3-6}$ cycloalkyl group, a $C_{6-10}$ aryl group optionally substituted by a halogen atom, or a ($C_{6-10}$ aryl) $C_{1-6}$ alkyl group, and
m denotes an integer from 0 to 2.].
(2) The prophylactic and/or therapeutic agent for inflammatory disease according to (1) above, wherein, in the formula (1), $R^4$ denotes a (($C_{3-6}$ cycloalkyl) ($C_{1-3}$ alkyl))amino group, L denotes a formula —$CH_2C(O)$—, o denotes 2, and m is 0.
(3) The prophylactic and/or therapeutic agent for inflammatory disease according to (1) or (2) above, wherein, in the formula (1), $R^4$ denotes a (cyclopropyl ($C_{1-3}$ alkyl))amino group.
(4) The prophylactic and/or therapeutic agent for inflammatory disease according to any one of (1) through (3) above, wherein the compound represented by the formula (1) is a compound represented by a formula (1') below:

[Chem. 3]

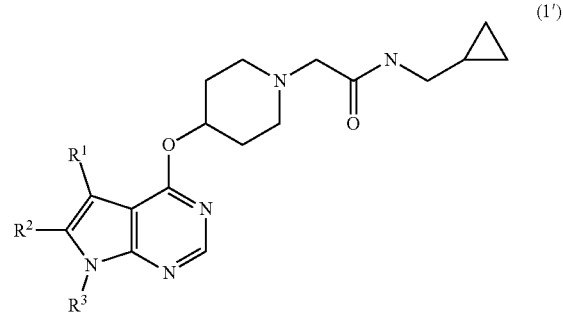

(1')

[where R¹, R², and R³ are same as respective definitions in the formula (1)].

(5) The prophylactic and/or therapeutic agent for inflammatory disease according to any one of (1) through (4) above, wherein the compound represented by the formula (1) is 2-[4-{(7-benzyl-5,6-dimethyl-7H-pyrrolo[2,3-d]pyrimidin-4-yl)oxy}piperidin-1-yl]-N(cyclopropylmethyl)acetamide.

(6) The prophylactic and/or therapeutic agent for inflammatory disease according to any one of (1) through (4) above, wherein the compound represented by the formula (1) is 2-[4-{(7-cyclohexyl-5,6-dimethyl-7H-pyrrolo[2,3-d]pyrimidin-4-yl)oxy}piperidin-1-yl]-N-(cyclopropylmethyl)acetamide.

(7) The prophylactic and/or therapeutic agent for inflammatory disease according to any one of (1) through (3) above, wherein the compound represented by the formula (1) is a compound represented by a formula (1") below.

[Chem. 4]

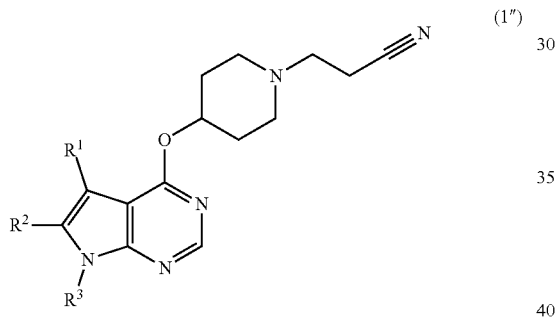

[where R¹, R², and R³ are the same as the respective definitions in the formula (1)].

(8) The prophylactic and/or therapeutic agent for inflammatory disease according to (1) or (7) above, wherein the compound represented by the formula (1) is 3-[4-{(7-cyclopentyl-5,6-dimethyl-7H-pyrrolo[2,3-d]pyrimidin-4-yl)oxy}piperidin-1-yl]propanenitrile.

(9) The prophylactic and/or therapeutic agent according to any one of (1) through (8) above, wherein the inflammatory disease is an autoimmune disease.

(10) The prophylactic and/or therapeutic agent according to (9) above, wherein the autoimmune disease is Sjögren syndrome or systemic lupus erythematosus.

(11) The prophylactic and/or therapeutic agent according to (9) or (10) above, wherein the autoimmune disease is Sjögren syndrome.

(12) The prophylactic and/or therapeutic agent according to any one of (9) through (11) above, wherein Sjögren syndrome is primary Sjögren syndrome.

(13) The prophylactic and/or therapeutic agent according to any one of (1) through (12) above, wherein the prophylactic and/or therapeutic agent is an oral agent.

(14) The prophylactic and/or therapeutic agent according to any one of (1) through (12) above, wherein the prophylactic and/or therapeutic agent is a parenteral agent.

(15) The prophylactic and/or therapeutic agent according to (14) above, wherein the parenteral agent is an injection.

(16) The prophylactic and/or therapeutic agent according to (14) above, wherein the parenteral agent is an ophthalmic preparation or a nasal preparation.

(17) The prophylactic and/or therapeutic agent according to (14) above, wherein the parenteral agent is an ointment, a cream, a lotion, a gel preparation, or a spray.

(18) A method of inhibiting inflammatory cytokine production, comprising administering a compound or a salt thereof, or a solvate thereof, the compound represented by a formula (1) below:

[Chem. 1]

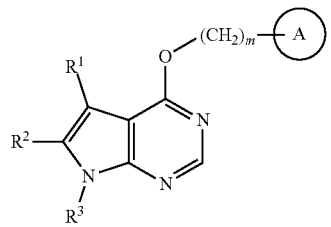

[where a ring A denotes a group represented by a formula (A) below

[Chem. 2]

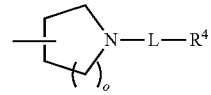

(where $R^4$ denotes a (($C_{3-6}$ cycloalkyl) ($C_{1-3}$ alkyl)) amino or nitrile group, L denotes a formula —$(CH_2)_n$—, —$CH_2C(O)$—, or —$C(O)CH_2$—, n denotes an integer from 0 to 3, and o denotes a natural number from 1 to 3), $R^1$ and $R^2$, being same or different from each other, denote a hydrogen atom or a $C_{1-6}$ alkyl group, $R^3$ denotes a $C_{3-6}$ cycloalkyl group, a $C_{6-10}$ aryl group optionally substituted by a halogen atom, or a ($C_{6-10}$ aryl) $C_{1-6}$ alkyl group, and m denotes an integer from 0 to 2.].

(19) The method according to (18) above, wherein, in the formula (1), $R^4$ denotes a (($C_{3-6}$ cycloalkyl) ($C_{1-3}$ alkyl))amino group, L denotes a formula —$CH_2C(O)$—, o denotes 2, and m is 0.

(20) The prophylactic and/or therapeutic agent for inflammatory disease according to (18) or (19) above, wherein, in the formula (1), $R^4$ denotes a (cyclopropyl ($C_{1-3}$ alkyl))amino group.

(21) The method according to any one of (18) through (20) above, wherein the compound represented by the formula (1) is a compound represented by a formula (1') below:

[Chem. 3]

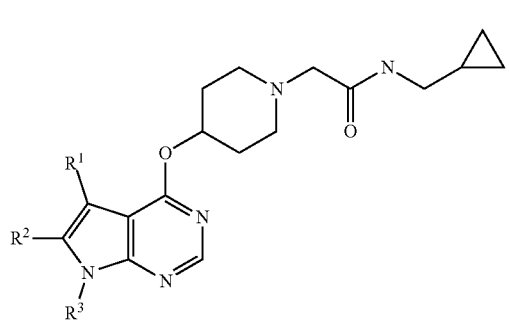

(1')

[where R¹, R², and R³ are the same as the respective definitions in the formula (1)].

(22) The method according to any one of (18) through (21) above, wherein the compound represented by the formula (1) is 2-[4-{(7-benzyl-5,6-dimethyl-7H-pyrrolo[2,3-d]pyrimidin-4-yl)oxy}piperidin-1-yl]-N(cyclopropylmethyl)acetamide.

(23) The method according to any one of (18) through (21) above, wherein the compound represented by the formula (1) is 2-[4-{(7-cyclohexyl-5,6-dimethyl-7H-pyrrolo[2,3-d]pyrimidin-4-yl)oxy}piperidin-1-yl]-N-(cyclopropylmethyl)acetamide.

(24) The method according to (18) above, wherein the compound represented by the formula (1) is a compound represented by a formula (1″) below:

[Chem. 4]

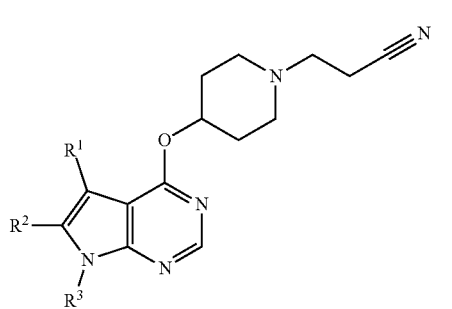

(1″)

[where R¹, R², and R³ are the same as the respective definitions in the formula (1)].

(25) The method according to (18) or (24) above, wherein the compound represented by the formula (1) is 3-[4-{(7-cyclopentyl-5,6-dimethyl-7H-pyrrolo[2,3-d]pyrimidin-4-yl)oxy}piperidin-1-yl]propanenitrile.

(26) The method according to any one of (18) through (25) above, wherein the inflammatory cytokine is IL-6.

(27) The method according to any one of (18) through (26) above, wherein the method is performed in vitro.

(28) A method of inhibiting IgG antibody production by an activated B cell, comprising administering a compound or a salt thereof, or a solvate thereof, the compound represented by a formula (1) below.

[Chem. 1]

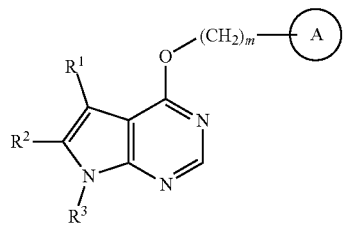

(1)

[where a ring A denotes a group represented by a formula (A) below

[Chem. 2]

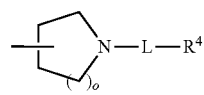

(A)

(where $R^4$ denotes a (($C_{3-6}$ cycloalkyl) ($C_{1-3}$ alkyl)) amino or nitrile group, L denotes a formula —$(CH_2)_n$—, —$CH_2C(O)$—, or —$C(O)CH_2$—, n denotes an integer from 0 to 3, and o denotes a natural number from 1 to 3), $R^1$ and $R^2$, being same or different from each other, denote a hydrogen atom or a $C_{1-6}$ alkyl group, $R^3$ denotes a $C_{3-6}$ cycloalkyl group, a $C_{6-10}$ aryl group optionally substituted by a halogen atom, or a ($C_{6-10}$ aryl) $C_{1-6}$ alkyl group, and m denotes an integer from 0 to 2.].

(29) The method according to (28) above, wherein, in the formula (1), $R^4$ denotes a (($C_{3-6}$ cycloalkyl) ($C_{1-3}$ alkyl))amino group, L denotes a formula —$CH_2C(O)$—, o denotes 2, and m is 0.

(30) The method according to (28) or (29) above, wherein, in the formula (1), $R^4$ denotes a (cyclopropyl ($C_{1-3}$ alkyl))amino group.

(31) The method according to any one of (28) through (30) above, wherein the compound represented by the formula (1) is a compound represented by a formula (1′) below:

[Chem. 3]

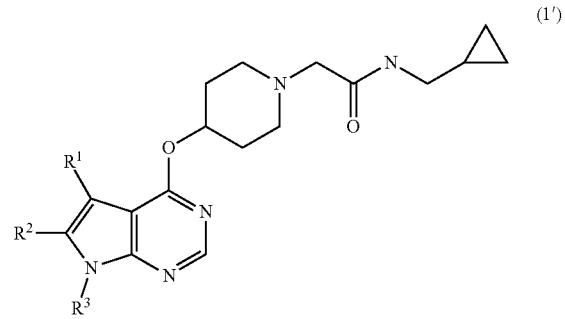

(1')

[where R¹, R², and R³ are the same as the respective definitions in the formula (1)].

(32) The method according to any one of (28) through (31) above, wherein the compound represented by the formula (1) is 2-[4-{(7-benzyl-5,6-dimethyl-7H-pyrrolo[2,3-d]pyrimidin-4-yl)oxy}piperidin-1-yl]-N(cyclopropylmethyl)acetamide.
(33) The method according to any one of (28) through (31) above, wherein the compound represented by the formula (1) is 2-[4-{(7-cyclohexyl-5,6-dimethyl-7H-pyrrolo[2,3-d]pyrimidin-4-yl)oxy}piperidin-1-yl]-N-(cyclopropylmethyl)acetamide.
(34) The method according to (28) above, wherein the compound represented by the formula (1) is a compound represented by a formula (1") below:

[Chem. 4]

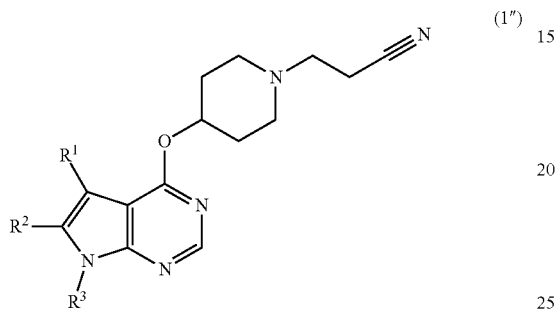

[where $R^1$, $R^2$, and $R^3$ are the same as the respective definitions in the formula (1)].
(35) The method according to (28) or (34) above, wherein the compound represented by the formula (1) is 3-[4-{(7-cyclopentyl-5,6-dimethyl-7H-pyrrolo[2,3-d]pyrimidin-4-yl)oxy}piperidin-1-yl]propanenitrile.
(36) The method according to any one of (28) through (35) above, wherein the activated B cell is a B cell stimulated with a BAFF-stimulated peripheral blood monocyte.
(37) The method according to any one of (28) through (36) above, wherein the method is performed in vitro.
(38) Use of a compound, for producing a prophylactic and/or therapeutic agent for inflammatory disease, represented by a formula (1) below:

[Chem. 1]

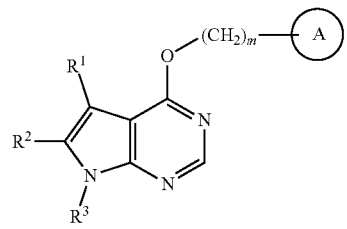

[where a ring A denotes a group represented by a formula (A) below

[Chem. 2]

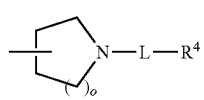

(where $R^4$ denotes a (($C_{3-6}$ cycloalkyl) ($C_{1-3}$ alkyl)) amino or nitrile group, L denotes a formula —$(CH_2)_n$—, —$CH_2C(O)$—, or —$C(O)CH_2$—, n denotes an integer from 0 to 3, and o denotes a natural number from 1 to 3), $R^1$ and $R^2$, being same or different from each other, denote a hydrogen atom or a $C_{1-6}$ alkyl group, $R^3$ denotes a $C_{3-6}$ cycloalkyl group, a $C_{6-10}$ aryl group optionally substituted by a halogen atom, or a ($C_{6-10}$ aryl) $C_{1-6}$ alkyl group, and m denotes an integer from 0 to 2.].

(39) The use according to (38) above, wherein, in the formula (1), $R^4$ denotes a (($C_{3-6}$ cycloalkyl) ($C_{1-3}$ alkyl))amino group, L denotes a formula —$CH_2C(O)$—, o denotes 2, and m is 0.
(40) The use according to (38) or (39) above, wherein, in the formula (1), $R^4$ denotes a (cyclopropyl ($C_{1-3}$ alkyl)) amino group.
(41) The use according to any one of (38) through (40) above, wherein the compound represented by the formula (1) is a compound represented by a formula (1') below:

[Chem. 3]

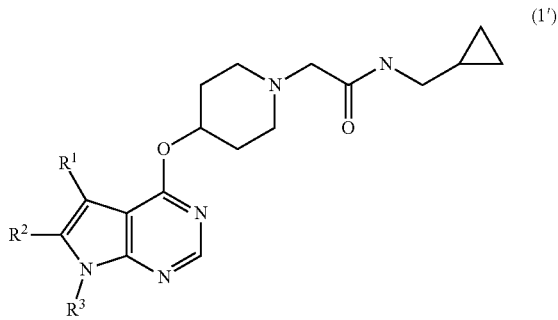

[where $R^1$, $R^2$, and $R^3$ are the same as the respective definitions in the formula (1)].

(42) The use according to any one of (38) through (41) above, wherein the compound represented by the formula (1) is 2-[4-{(7-benzyl-5,6-dimethyl-7H-pyrrolo[2,3-d]pyrimidin-4-yl)oxy}piperidin-1-yl]-N(cyclopropylmethyl)acetamide.
(43) The use according to any one of (38) through (41) above, wherein the compound represented by the formula (1) is 2-[4-{(7-cyclohexyl-5,6-dimethyl-7H-pyrrolo[2,3-d]pyrimidin-4-yl)oxy}piperidin-1-yl]-N-(cyclopropylmethyl)acetamide.
(44) The use according to (38) above, wherein the compound represented by the formula (1) is a compound represented by a formula (1") below:

[Chem. 4]

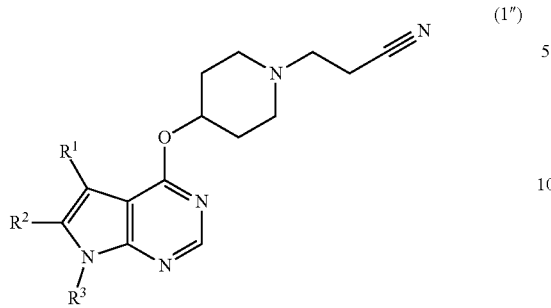

(1″)

[where $R^1$, $R^2$, and $R^3$ are the same as the respective definitions in the formula (1)].

(45) The use according to (38) or (44) above, wherein the compound represented by the formula (1) is 3-[4-{(7-cyclopentyl-5,6-dimethyl-7H-pyrrolo[2,3-d]pyrimidin-4-yl)oxy}piperidin-1-yl]propanenitrile.

(46) The prophylactic and/or therapeutic agent according to any one of (38) through (45) above, wherein the inflammatory disease is an autoimmune disease.

(47) The use according to (46) above, wherein the autoimmune disease is Sjögren syndrome or systemic lupus erythematosus.

(48) The use according to (46) or (47) above, wherein the autoimmune disease is Sjögren syndrome.

(49) A compound, for use in a prophylactic and/or therapeutic method for inflammatory disease, represented by a formula (1) below.

[Chem. 1]

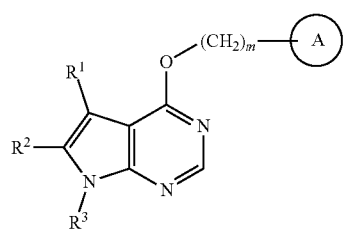

(1)

[where a ring A denotes a group represented by a formula (A) below

[Chem. 2]

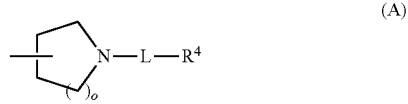

(A)

(where $R^4$ denotes a (($C_{3-6}$ cycloalkyl) ($C_{1-3}$ alkyl)) amino or nitrile group, L denotes a formula —$(CH_2)_n$—, —$CH_2C(O)$—, or —$C(O)CH_2$—, n denotes an integer from 0 to 3, and o denotes a natural number from 1 to 3), $R^1$ and $R^2$, being same or different from each other, denote a hydrogen atom or a $C_{1-6}$ alkyl group, $R^3$ denotes a $C_{3-6}$ cycloalkyl group, a $C_{6-10}$ aryl group optionally substituted by a halogen atom, or a ($C_{6-10}$ aryl) $C_{1-6}$ alkyl group, and m denotes an integer from 0 to 2.].

(50) The compound according to (49) above, wherein, in the formula (1), $R^4$ denotes a (($C_{3-6}$ cycloalkyl) ($C_{1-3}$ alkyl))amino group, L denotes a formula —$CH_2C(O)$—, o denotes 2, and m is 0.

(51) The compound according to (49) or (50) above, wherein, in the formula (1), $R^4$ denotes a (cyclopropyl ($C_{1-3}$ alkyl))amino group.

(52) The compound according to any one of (49) through (51) above, wherein the compound represented by the formula (1) is a compound represented by a formula (1') below:

[Chem. 3]

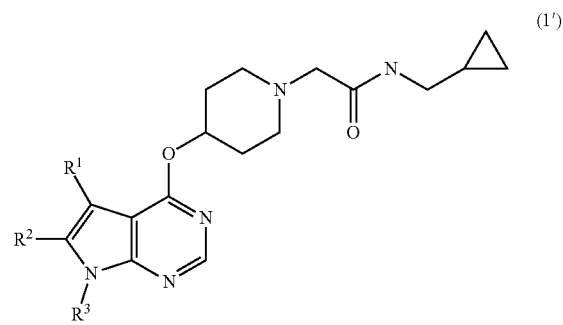

(1')

[where $R^1$, $R^2$, and $R^3$ are the same as the respective definitions in the formula (1)].

(53) The compound according to any one of (49) through (52) above, wherein the compound represented by the formula (1) is 2-[4-{(7-benzyl-5,6-dimethyl-7H-pyrrolo[2,3-d]pyrimidin-4-yl)oxy}piperidin-1-yl]-N(cyclopropylmethyl)acetamide.

(54) The compound according to any one of (49) through (52) above, wherein the compound represented by the formula (1) is 2-[4-{(7-cyclohexyl-5,6-dimethyl-7H-pyrrolo[2,3-d]pyrimidin-4-yl)oxy}piperidin-1-yl]-N-(cyclopropylmethyl)acetamide.

(55) The compound according to (49) above, wherein the compound represented by the formula (1) is a compound represented by a formula (1″) below:

[Chem. 4]

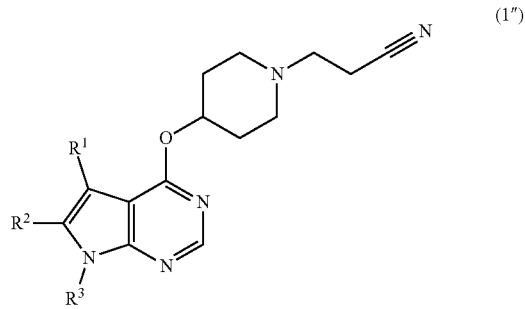

(1″)

[where $R^1$, $R^2$, and $R^3$ are the same as the respective definitions in the formula (1)].

(56) The compound according to (49) or (55) above, wherein the compound represented by the formula (1) is 3-[4-{(7-cyclopentyl-5,6-dimethyl-7H-pyrrolo[2,3-d]pyrimidin-4-yl)oxy}piperidin-1-yl]propanenitrile.

(57) The compound according to any one of (49) through (56) above, wherein the inflammatory disease is an autoimmune disease.

(58) The compound according to (57) above, wherein the autoimmune disease is Sjögren syndrome or systemic lupus erythematosus.

(59) The compound according to (57) or (58) above, wherein the autoimmune disease is Sjögren syndrome.

(60) A prophylactic and/or therapeutic method for inflammatory disease, comprising administering a pharmaceutical composition containing an effective dose of a pyrrolopyrrolidine compound to a subject in need thereof, wherein the pyrrolopyrrolidine compound is represented by a formula (1) below:

[Chem. 1]

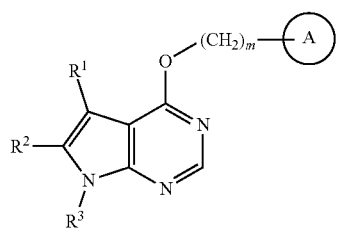

(1)

[where a ring A denotes a group represented by a formula (A) below

[Chem. 2]

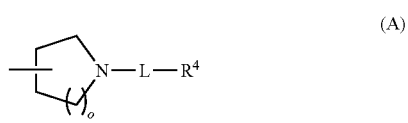

(A)

(where $R^4$ denotes a (($C_{3-6}$ cycloalkyl) ($C_{1-3}$ alkyl)) amino or nitrile group, L denotes a formula —$(CH_2)_n$—, —$CH_2C(O)$—, or —$C(O)CH_2$—, n denotes an integer from 0 to 3, and o denotes a natural number from 1 to 3), $R^1$ and $R^2$, being same or different from each other, denote a hydrogen atom or a $C_{1-6}$ alkyl group, $R^3$ denotes a $C_{3-6}$ cycloalkyl group, a $C_{6-10}$ aryl group optionally substituted by a halogen atom, or a ($C_{6-10}$ aryl) $C_{1-6}$ alkyl group, and m denotes an integer from 0 to 2.].

(61) The method according to (60) above, wherein, in the formula (1), $R^4$ denotes a (($C_{3-6}$ cycloalkyl) ($C_{1-3}$ alkyl))amino group, L denotes a formula —$CH_2C(O)$—, o denotes 2, and m is 0.

(62) The method according to (60) or (61) above, wherein, in the formula (1), $R^4$ denotes a (cyclopropyl ($C_{1-3}$ alkyl))amino group.

(63) The method according to any one of (60) through (62) above, wherein the compound represented by the formula (1) is a compound represented by a formula (1') below:

[Chem. 3]

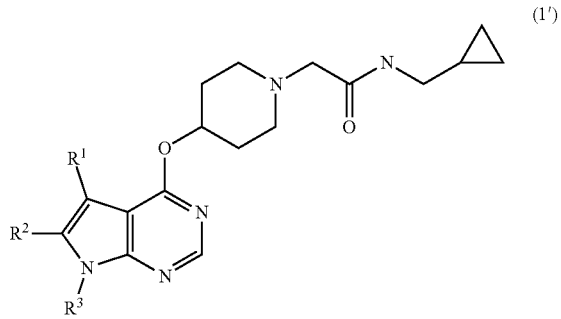

(1')

[where $R^1$, $R^2$, and $R^3$ are the same as the respective definitions in the formula (1)].

(64) The method according to any one of (60) through (63) above, wherein the compound represented by the formula (1) is 2-[4-{(7-benzyl-5,6-dimethyl-7H-pyrrolo[2,3-d]pyrimidin-4-yl)oxy}piperidin-1-yl]-N(cyclopropylmethyl)acetamide.

(65) The method according to any one of (60) through (63) above, wherein the compound represented by the formula (1) is 2-[4-{(7-cyclohexyl-5,6-dimethyl-7H-pyrrolo[2,3-d]pyrimidin-4-yl)oxy}piperidin-1-yl]-N-(cyclopropylmethyl)acetamide.

(66) The method according to (60) above, wherein the compound represented by the formula (1) is a compound represented by a formula (1") below:

[Chem. 4]

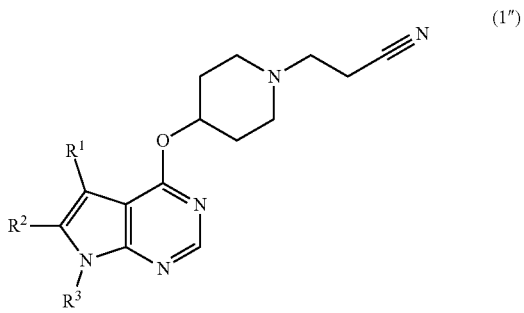

(1")

[where $R^1$, $R^2$, and $R^3$ are the same as the respective definitions in the formula (1)].

(67) The method according to (60) or (66) above, wherein the compound represented by the formula (1) is 3-[4-{(7-cyclopentyl-5,6-dimethyl-7H-pyrrolo[2,3-d]pyrimidin-4-yl)oxy}piperidin-1-yl]propanenitrile.

(68) The method according to any one of (60) through (67) above, wherein the inflammatory disease is an autoimmune disease.

(69) The method according to (68) above, wherein the autoimmune disease is Sjögren syndrome or systemic lupus erythematosus.

(70) The method according to any one of (60) through (67) above, wherein the subject is a patient with an inflammatory disease.

(71) The method according to (68) above, wherein the subject is a patient with an autoimmune disease.

(72) The method according to (69) above, wherein the subject is a patient with Sjögren syndrome or systemic lupus erythematosus.

Advantageous Effects of Invention

The prophylactic and/or therapeutic agent for inflammatory disease containing, as an active ingredient, the pyrrolopyrimidine compound of the present invention, typically 2-[4-{(7-benzyl-5,6-dimethyl-7H-pyrrolo[2,3-d]pyrimidin-4-yl)oxy}piperidin-1-yl]-N(cyclopropylmethyl)acetamide, is thus capable of effectively prevent or treat inflammatory diseases. Although the inflammatory diseases are not particularly limited as long as the diseases are based on systemic or organ specific inflammatory response, examples of such a disease include autoimmune diseases characterized by autoantibody production and/or diseases with enhancement of cellular function induced by BAFF and an increase in the production of IL-6, which is inflammatory cytokine. In particular, the pyrrolopyrimidine compound of the present invention is capable of preventing or treating Sjögren syndrome and/or systemic lupus erythematosus. An example of Sjögren syndrome includes primary Sjögren syndrome. The method including administering the pyrrolopyrimidine compound of the present invention, typically 2-[4-{(7-benzyl-5,6-dimethyl-7H-pyrrolo[2,3-d]pyrimidin-4-yl)oxy}piperidin-1-yl]-N(cyclopropylmethyl)acetamide, is capable of inhibiting enhancement of inflammatory cytokine IL-6 production by cells responding to BAFF stimuli and inhibiting enhancement of IgG antibody production by B cells responding to BAFF stimuli. The method including administering the pyrrolopyrimidine compound of the present invention, typically 2-[4-{(7-benzyl-5,6-dimethyl-7H-pyrrolo[2,3-d]pyrimidin-4-yl)oxy}piperidin-1-yl]-N(cyclopropylmethyl)acetamide, is capable of inhibiting production of autoantibodies in vivo (specific examples include anti-dsDNA antibodies) and inhibiting inflammatory response of biological tissues (specific examples include lymphocyte infiltration into tissues). In the present invention, the screening system based on the amount of IL-6 production, as an index, using the monocytic cell line to select 2-[4-{(7-benzyl-5,6-dimethyl-7H-pyrrolo[2,3-d]pyrimidin-4-yl)oxy}piperidin-1-yl]-N(cyclopropylmethyl)acetamide is to find a compound with partial or complete cancel action on the enhancing effect of BAFF, and thus the screening system is useful as a pharmaceutical compound selection system not only for Sjögren syndrome but also various inflammatory diseases associated with the action of BAFF, such as systemic lupus erythematosus. At the same time, of course, it is possible to widely use a compound or a salt thereof, or a solvate thereof, the compound represented by the formula (1) and typically 2-[4-{(7-benzyl-5,6-dimethyl-7H-pyrrolo[2,3-d]pyrimidin-4-yl)oxy}piperidin-1-yl]-N(cyclopropylmethyl)acetamide, which is a compound found by the screening system of the present invention, for prophylactic and therapeutic purposes against various inflammatory diseases associated with BAFF.

BRIEF DESCRIPTION OF THE DRAWINGS

FIG. 1A is a diagram illustrating experimental results of measuring the amounts of IL-6 production on the third day of culture in the case of adding (0.04 µM, 0.2 µM, and 1 µM) 2-[4-{(7-benzyl-5,6-dimethyl-7H-pyrrolo[2,3-d]pyrimidin-4-yl)oxy}piperidin-1-yl]-N(cyclopropylmethyl)acetamide (hereinafter, may be referred to as "Compound A") together with human BAFF and the case of not adding (control) in a culture system where human monocytic cell line THP-1 was precultured for four days in the presence of 200 ng/mL IFNγ and then cultured in the presence of 2 µg/mL human BAFF. The amounts of IL-6 production were determined by ELISA using culture supernatant. For analysis of the amounts of IL-6 production, the quantitative value of the amount of IL-6 production in the case of not adding BAFF after IFNγ stimuli was subtracted from the determined value in each case to calculate a relative value based on 100% of the differential value in the case of control. A bar height indicates an average value (%) of the amounts of IL-6 production (relative values) together with the standard deviation. In FIG. 1A, *** denotes that a significant decline in the amount of IL-6 production ($p<0.001$) was found in the case of adding Compound A compared with the case of adding no Compound A (control).

FIG. 1B is a diagram illustrating experimental results of measuring the amounts of IL-6 production on the third day of culture in the case of adding (0.04 µM, 0.2 µM, and 1 µM) 3-[4-{(7-cyclopentyl-5,6-dimethyl-7H-pyrrolo[2,3-d]pyrimidin-4-yl)oxy}piperidin-1-yl]propanenitrile (hereinafter, may be referred to as "Compound B") together with human BAFF and the case of not adding (control) in a culture system where human monocytic cell line THP-1 was precultured for four days in the presence of 200 ng/mL IFNγ and then cultured in the presence of 2 µg/mL human BAFF. The amounts of IL-6 production were determined by ELISA using culture supernatant. For analysis of the amounts of IL-6 production, the quantitative value of the amount of IL-6 production in the case of not adding BAFF after IFNγ stimuli was subtracted from the determined value in each case to calculate a relative value based on 100% of the differential value in the case of control. A bar height indicates an average value (%) of the amounts of IL-6 production (relative values) together with the standard deviation. In FIG. 1B, *** denotes that a significant decline in the amount of IL-6 production ($p<0.001$) was found in the case of adding Compound B compared with the case of adding no Compound B (control).

FIG. 1C is a diagram illustrating experimental results of measuring the amounts of IL-6 production on the third day of culture in the case of adding (1.2 µM, 6 µM, and 30 µM) 1-(2-[4-{7-cyclopentyl-5,6-dimethyl-7H-pyrrolo[2,3-d]pyrimidin-4-yl)oxy}piperidin-T-yl]-2-oxoethyl)pyrrolidine-2-one (hereinafter, may be referred to as "BIK-13") together with human BAFF and the case of not adding (control) in the same culture system as FIG. 1A where human monocytic cell line THP-1 was precultured for four days in the presence of 200 ng/mL IFNγ and then cultured in the presence of 2 µg/mL human BAFF. The amounts of IL-6 production were determined by ELISA using culture supernatant. For analysis of the amounts of IL-6 production, the quantitative value of the amount of IL-6 production in the case of not adding BAFF after IFNγ stimuli was subtracted from the determined value in each case to calculate a relative value based on 100% of the differential value in the case of control. A bar height indicates an average value (%) of the amounts of IL-6 production (relative values) together with the standard deviation. In FIG. 1C, *** denotes that a significant decline in the amount of IL-6 production ($p<0.001$) was found in the case of adding BIK-13 compared with the case of adding no BIK-13 (control).

FIG. 2 is a diagram illustrating experimental results of measuring the amounts of IL-6 production on the fourth day of culture in the case of adding (2 µM and 10 µM) Compound A together with human BAFF, the case of adding (2 µM and 10 µM) BIK-13 together with human BAFF, and the case of adding neither (control) in a culture system where human peripheral blood monocytes collected from normal healthy individuals was cultured in the presence of 2 µg/mL human BAFF. The amounts of IL-6 production were determined by ELISA using culture supernatant. For analysis of the amounts of IL-6 production, a relative value was calculated based on 100% in the case of control. A bar height indicates an average value (%) of the amounts of IL-6 production (relative values) together with the standard deviation. In FIG. 2, *** denotes that a significant decline in the amount of IL-6 production ($p<0.001$) was found in the case of adding Compound A compared with the case of control. In addition, * denotes that a significant decline in the amount of IL-6 production ($p<0.05$) was found in the case of adding BIK-13 compared with the case of control.

FIG. 3 is a diagram illustrating experimental results of measuring the amounts of IgG antibody production on the fourth day of culture in the case of adding no BAFF and no compounds (B+mono), the case of adding 2 μg/mL human BAFF (B+mono+BAFF), the case of adding (1 μM and 10 μM) Compound A together with human BAFF (1 and 10), and the case of adding (1 μM and 10 μM) BIK-13 together with human BAFF (1 and 10) in a coculture system where human peripheral blood monocytes and B cells isolated from peripheral blood derived from Sjögren syndrome patients were separately seeded and cultured via a membrane in Transwell® plates. The amounts of IgG antibody production were determined by ELISA using culture supernatant. For analysis of the amounts of IgG antibody production, a relative value was calculated based on 100% in the case of the presence of BAFF/the absence of the compounds (B+mono+BAFF). A bar height indicates an average value (%) of the amounts of IgG antibody production (relative values) together with the standard deviation. In FIG. 3,  denotes that a significant decline in the amount of IgG antibody production ($p<0.01$) in the case of adding 1 μM Compound A and the case of adding 10 μM BIK-13 compared with the case of (B+mono+BAFF). In addition, * denotes that a significant decline in the amount of IgG antibody production ($p<0.001$) was found in the case of adding 10 μM Compound A compared with the case of (B+mono+BAFF).

FIG. 4 is a diagram illustrating experimental results of measuring the amounts of IgG antibody production on the seventh day of culture in the case of adding no compounds without stimuli (none), the case of not adding Compound A with stimuli (5 μg/mL anti-human IgM antibody, 1 μg/mL anti-human CD40 antibody, 30 ng/mL human IL-21, and 30 ng/mL human BAFF) (control), and the case of adding Compound A (0.4 μM, 2 μM, and 10 μM) together with the above stimuli (0.4 μM, 2 μM, and 10 μM) in a culture system where peripheral blood mononuclear cells isolated from human peripheral blood from normal healthy individuals were cultured. The amounts of IgG antibody production were determined by ELISA using culture supernatant. For analysis of the amounts of IgG antibody production, a relative value was calculated based on 100% in the case of the presence of the above stimuli/the absence of Compound A (control). A bar height indicates an average value (%) of the amounts of IgG antibody production (relative values) together with the standard deviation. In FIG. 4, *, , and * respectively denote that a significant decline in the amount of IgG antibody production ($p<0.05$, $p<0.01$, and $p<0.001$) was found in the case of adding Compound A compared with the case of (control).

FIG. 5 is a diagram illustrating anti-dsDNA antibody titers in the blood in the case of administering a physiological saline solution (not administering Compound A) (saline) and the case of administering Compound A (0.04 mg/kg, 0.2 mg/kg, and 1 mg/kg) in MRL/lpr mice (female) as a disease model with a high incidence rate of inflammatory diseases, such as nephritis, vasculitis, and arthritis, causing multiple autoimmune phenomena (may also be referred to as a collagen disease model or a systemic lupus erythematosus model). The administration was initiated from nine weeks old (0 w) and performed five times a week for 16 weeks. The administration was performed by intravenous injection (i.p.). The anti-dsDNA antibody titers in the blood were measured by ELISA using the blood collected over time (0 w, 4 w, 8 w, 12 w, and 16 w). The abscissa represents the time elapsed since the initiation of administration and the ordinate represents the measurement (the number of units) of the absorbance corresponding to the anti-dsDNA antibody titer in the blood. In FIG. 5, * denotes that a significant decline in the anti-dsDNA antibody titer ($p<0.05$) was found in the case of administering Compound A (0.2 mg/kg and 1 mg/kg) at 16 w compared with the case of administering a physiological saline solution.

FIG. 6 is a diagram illustrating anti-dsDNA antibody titers in the blood in the case of administering a physiological saline solution (not administering Compound A) (saline) and the case of administering Compound A (0.2 mg/kg and 1 mg/kg) in NZB/WF1 mice (female) as a disease model producing anti-dsDNA antibodies with age and spontaneously developing glomerulonephritis (may also be referred to as a systemic lupus erythematosus model). The administration was initiated from 20 weeks old (0 w) and performed five times a week for 20 weeks. The administration was performed by intravenous injection (i.p.). The anti-dsDNA antibody titers in the blood were measured by ELISA using the blood collected over time (0 w, 4 w, 8 w, 12 w, and 16 w). The abscissa represents the time elapsed since the initiation of administration and the ordinate represents the measurement (the number of units) of the absorbance corresponding to the anti-dsDNA antibody titer in the blood. In FIG. 6, * denotes that a significant decline in the anti-dsDNA antibody titer ($p<0.05$) was found in the case of administering Compound A (1 mg/kg) at 12 w and 16 w compared with the case of administering a physiological saline solution.

FIG. 7 is a diagram illustrating protein contents in the urine in the case of administering a physiological saline solution (not administering Compound A) (saline) and the case of administering Compound A (0.2 mg/kg and 1 mg/kg) in NZB/WF1 mice (female). The administration was initiated from 20 weeks old (0 w) and performed five times a week for 20 weeks. The administration was performed by intravenous injection (i.p.). The protein contents in the urine were evaluated by numerically expressing the reaction on the test strips using the urine collected over time (0 w, 4 w, 7 w, 12 w, 16 w, and 18 w) and urine protein test strips. The abscissa represents the time elapsed since the initiation of administration and the ordinate represents the evaluation value of the protein contents in the urine. In FIG. 7, * denotes that a significant decline in the protein content in the urine ($p<0.05$) was found in the case of administering Compound A at 12 w (1 mg/kg) and 18 w (0.2 mg/kg and 1 mg/kg) compared with the case of administering a physiological saline solution.

FIG. 8A illustrates microscopically observed images of lacrimal gland tissues by hematoxylin-eosin staining in the case of administering a physiological saline solution (not administering Compound A) (saline) and the case of administering Compound A (0.04 mg/kg, 0.2 mg/kg, and 1 mg/kg) in MRL/lpr mice (female). The administration was initiated from nine weeks old and performed five times a week for 16 weeks. The administration was performed by intravenous injection (i.p.). Tissue samples were collected by dissecting 25-week-old mice after administration in the 16th week. In each panel, the bar indicates 1 mm.

FIG. 8B illustrates microscopically observed images of submandibular gland tissues by hematoxylin-eosin staining in the case of administering a physiological saline solution (not administering Compound A) (saline) and the case of administering Compound A (0.04 mg/kg, 0.2 mg/kg, and 1 mg/kg) in MRL/lpr mice (female). The administration was initiated from nine weeks old and performed five times a week for 16 weeks. The administration was performed by intravenous injection (i.p.). Tissue samples were collected by dissecting 25-week-old mice after administration in the 16th week. In each panel, the bar indicates 1 mm.

FIG. 8C illustrates microscopically observed images of kidney tissues by hematoxylin-eosin staining in the case of administering a physiological saline solution (not administering Compound A) (saline) and the case of administering Compound A (0.04 mg/kg, 0.2 mg/kg, and 1 mg/kg) in MRL/lpr mice (female). The administration was initiated from nine weeks old and performed five times a week for 16 weeks. The administration was performed by intravenous injection (i.p.). Tissue samples were collected by dissecting 25-week-old mice after administration in the 16th week. In each panel, the bar indicates 1 mm.

DESCRIPTION OF EMBODIMENTS

A prophylactic and/or therapeutic agent for inflammatory diseases of the present invention is prepared as a pharmaceutical composition by combining, as an active ingredient, a predetermined amount of a compound represented by the formula (1) or a salt thereof, or a solvate thereof in the composition. A representative prophylactic and/or therapeutic agent for inflammatory diseases of the present invention is prepared as a pharmaceutical composition by combining 2-[4-{(7-benzyl-5,6-dimethyl-7H-pyrrolo[2,3-d]pyrimidin-4-yl)oxy}piperidin-1-yl]-N(cyclopropylmethyl)acetamide (Compound A) as an active ingredient. The compound of the formula (1) is defined as follows.

[Chem. 1]

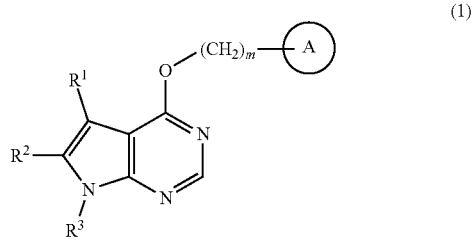

(1)

[where a ring A denotes a group represented by a formula (A) below

[Chem. 2]

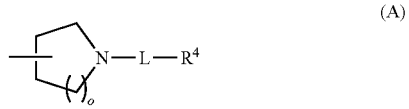

(A)

(where $R^4$ denotes a ((C$_{3-6}$ cycloalkyl) (C$_{1-3}$ alkyl)) amino or nitrile group, L denotes a formula —(CH$_2$)$_n$—, —CH$_2$C(O)—, or —C(O)CH$_2$—, n denotes an integer from 0 to 3, and o denotes a natural number from 1 to 3), $R^1$ and $R^2$, being same or different from each other, denote a hydrogen atom or a C$_{1-6}$ alkyl group, $R^3$ denotes a C$_{3-6}$ cycloalkyl group, a C$_{6-10}$ aryl group optionally substituted by a halogen atom, or a (C$_{6-10}$ aryl) C$_{1-6}$ alkyl group, and m denotes an integer from 0 to 2.].

The "C$_{1-6}$ alkyl group" used herein means a linear or branched hydrocarbon group having a carbon number from 1 to 6, preferably a chain saturated hydrocarbon group. Examples of the "C$_{1-6}$ alkyl group" include, but not particularly limited to, a methyl group, an ethyl group, an n-propyl group, an isopropyl group, an n-butyl group, an isobutyl group, a sec-butyl group, a tert-butyl group, an n-pentyl group, an isopentyl group, a neopentyl group, an n-hexyl group, an isohexyl group, and the like. It should be noted that the definition of "C$_{1-6}$ alkyl" is used for a "(C$_{1-6}$ alkyl)amino group" and the "(C$_{6-10}$ aryl) C$_{1-6}$ alkyl group" herein and the definition is the same as "C$_{1-6}$ alkyl" above.

Examples of the "(C$_{1-3}$ alkyl)amino group" used herein include amino groups mono- or di-substituted by a C$_{1-3}$ alkyl group. The examples include linear or branched alkylamino groups having a carbon number from 1 to 3, such as a methylamino group, an ethylamino group, an n-propyl amino group, and an isopropyl amino group.

"C$_{3-6}$ cycloalkyl" used herein means a saturated cyclic hydrocarbon group having a carbon number from 3 to 6. Examples of "C$_{3-6}$ cycloalkyl" include cyclopropyl, cyclobutyl, cyclopentyl, cyclohexyl, and the like.

Examples of the "((C$_{3-6}$ cycloalkyl) (C$_{1-3}$ alkyl))amino group" herein include amino groups monosubstituted by the "((C$_{3-6}$ cycloalkyl) (C$_{1-3}$ alkyl))" group. The examples of the "((C$_{3-6}$ cycloalkyl) (C$_{1-3}$ alkyl))amino group" include ((C$_{3-6}$ cycloalkyl) (C$_{1-3}$ alkyl))amino groups, such as a (cyclopropylmethyl)amino group, a (cyclopropylethyl)amino group, a (cyclopropylpropyl)amino group, a (cyclobutylmethyl) amino group, a (cyclopentylmethyl)amino group, a cyclohexylmethyl amino group, and the like.

The "C$_{6-10}$ aryl group" used herein means aromatic hydrocarbon groups having a carbon number from 6 to 10. Examples of the "C$_{6-10}$ aryl group" include a phenyl group, a naphthyl group, an azulenyl group, and the like. It should be noted that the definition of "C$_{6-10}$ aryl" is used for the "C$_{6-10}$ aryl group optionally substituted by a halogen atom" and the "(C$_{6-10}$ aryl) C$_{1-6}$ alkyl group" herein and the definition is the same as "C$_{6-10}$ aryl" above. Examples of the "halogen atom" include a fluorine atom, a chlorine atom, a bromine atom, an iodine atom, and the like.

Examples of the "(C$_{6-10}$ aryl) C$_{1-6}$ alkyl group" used herein means include C$_{1-6}$ alkyl groups substituted by one or more of the above "C$_{6-10}$ aryl groups". Examples of the "(C$_{6-10}$ aryl) C$_{1-6}$ alkyl group" include a benzyl group, a phenethyl group, a phenylpropyl group, a phenylbutyl group, a phenylpentyl group, a phenylhexyl group, a naphthylmethyl group, a naphthylethyl group, a naphthylpropyl group, a naphthylbutyl group, an azulenylmethyl group, an azulenylethyl group, an azulenylpropyl group, an azulenylbutyl group, and the like.

Examples of the "C$_{6-10}$ aryl group optionally substituted by a halogen atom" include C$_{6-10}$ aryl groups substituted by one or more halogen atoms. Examples of such a C$_{6-10}$ aryl group substituted by one or more halogen atoms include a halogen-substituted phenyl group, a halogen-substituted naphthyl group, a halogen-substituted azulenyl group, and the like, and more preferred examples include phenyl groups substituted at the fourth position by a halogen atom and the like.

In the formula (1), the "$C_{1-6}$ alkyl group" in $R^1$ and $R^2$ is preferably a $C_{1-4}$ alkyl group and more preferably a methyl group.

In the formula (1), the "$C_{3-6}$ cycloalkyl group" in $R^3$ is preferably a $C_{5-6}$ cycloalkyl group and more preferably a cyclopentyl group or a cyclohexyl group. In particular, a cyclopentyl group is preferred.

In the formula (1), the "$C_{6-10}$ aryl group optionally substituted by a halogen atom" is preferably a phenyl group or a 4-fluorophenyl group.

In the formula (1), the "($C_{6-10}$ aryl) $C_{1-6}$ alkyl group" is preferably a phenyl-substituted $C_{1-6}$ alkyl group and more preferably a benzyl group.

In the formula (1), the "(($C_{3-6}$ cycloalkyl) ($C_{1-3}$ alkyl)) amino group" in $R^4$ is preferably a (($C_{3-4}$ cycloalkyl)methyl) amino group or a (($C_{3-4}$ cycloalkyl)ethyl)amino group and more preferably a(cyclopropylmethyl)amino group or a cyclopropylethyl)amino group. In particular, a (cyclopropylmethyl)amino group is preferred.

Preferred examples of the compound represented by the formula (1) include a compound represented by a formula (1') below:

[Chem. 3]

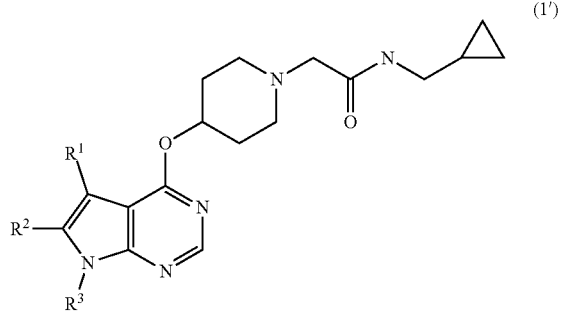

(1')

[where $R^1$, $R^2$, and $R^3$ are the same as the respective definitions in the formula (1)].

Representative examples of the compound represented by the formula (1') include 2-[4-{(7-benzyl-5,6-dimethyl-7H-pyrrolo[2,3-d]pyrimidin-4-yl)oxy}piperidin-1-yl]-N(cyclopropylmethyl)acetamide and 2-[4-{(7-cyclohexyl-5,6-dimethyl-7H-pyrrolo[2,3-d]pyrimidin-4-yl)oxy}piperidin-1-yl]-N-(cyclopropylmethyl)acetamide.

Another preferred example of the compound represented by the formula (1) includes a compound represented by a formula (1") below.

[Chem. 4]

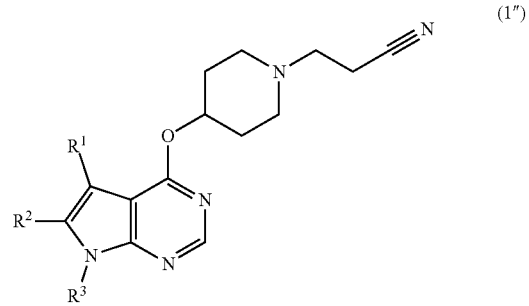

(1")

[where $R^1$, $R^2$, and $R^3$ are the same as the respective definitions in the formula (1)].

Representative examples of the compound represented by the formula (1") include 3-[4-{(7-cyclopentyl-5,6-dimethyl-7H-pyrrolo[2,3-d]pyrimidin-4-yl)oxy}piperidin-1-yl]propanenitrile.

The pyrrolopyrimidine compound represented by the formula (1) of the present invention or a salt thereof, or a solvate thereof includes not only the pyrrolopyrimidine compound of the present invention but also pharmaceutically acceptable salts thereof, various hydrates, solvates, and polymorphic materials thereof, and prodrugs for these materials. In the case of containing an asymmetric carbon atom, the compound includes not only the racemic form but also the optically active form.

Specific examples of the salts acceptable as the pyrrolopyrimidine compound represented by the formula (1) of the present invention include acid addition salts and the like with, in the case of using the compound as a basic compound, inorganic acids (e.g., hydrochloric acid, hydrobromic acid, hydroiodic acid, sulfuric acid, nitric acid, phosphoric acid, etc.) and organic acids (e.g., methanesulfonic acid, ethanesulfonic acid, p-toluenesulfonic acid, etc.). Meanwhile, examples of the salts include, in the case of using the compound as an acidic compound, inorganic salts (e.g., sodium salt, potassium salt, lithium salt, barium salt, calcium salt, magnesium salt, etc.) and the like.

Examples of the solvates of the pyrrolopyrimidine compound represented by the formula (1) of the present invention and the pharmaceutically acceptable salts thereof include hydrates and various solvates (e.g., solvates with alcohols, such as ethanol).

The pyrrolopyrimidine compound represented by the formula (1) of the present invention may be produced with reference to known methods described in JP 8-53454 A, Heterocycles, 39(1), 345-356 (1994), and the like. For example, it may be produced by, but not limited to, the method illustrated in the following reaction scheme or methods analogous to this. Each reaction may be performed by protecting functional groups as needed. The protection and deprotection conditions may refer to generally used methods (Protective Groups in Organic Synthesis Third Edition, John Wiley & Sons, Inc.).

Method A: Compound 1a May be Produced by the Following Method.

[Reaction Scheme 1]

[Chem. 5]

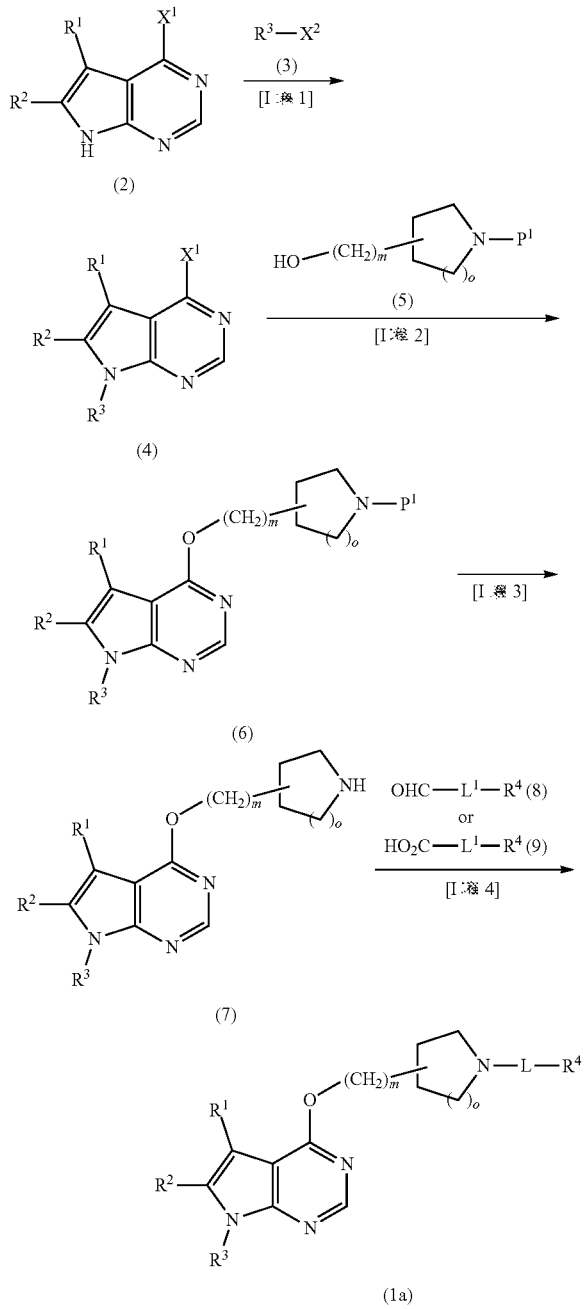

[where $R^1$, $R^2$, $R^4$, L, m, and o denote the same definitions as above, $R^3$ denotes a $C_{3-6}$ cycloalkyl group or a $(C_{6-10}$ aryl) $C_{1-6}$ alkyl group, $P^1$ denotes a protecting group for the amino group (a benzyl group, a benzyloxycarbonyl group, a tert-butoxycarbonyl group, etc.), $X^1$ and $X^2$ denote leaving groups, such as a halogen atom, $L^1$ denotes —$(CH_2)_p$—, and p denotes an integer from 0 to 2.]

Step 1: Compound (2) and Compound (3) are reacted in the presence of base in a solvent to produce Compound (4). In this step, although the amount of Compound (3) is not particularly limited, for example, from 1.0 to 1.5 Compound (2) equivalents may be used for reaction. Although the amount of the base is not particularly limited, for example, from 1.0 to 1.5 Compound (2) equivalents may be used for reaction. Although the solvent used in this step is not particularly limited as long as the solvent does not inhibit the reaction, examples of the solvent include: amides, such as N,N-dimethylformamide and N,N-dimethylacetamide; ethers, such as diethyl ether, diisopropyl ether, tetrahydrofuran, dioxane, and ethylene glycol dimethyl ether; halogenated hydrocarbons, such as dichloromethane and 1,2-dichloromethane; and the like. Examples of the base to be used include, but not particularly limited to: organic bases, such as pyridine, 4-dimethylaminopyridine (DMAP), collidine, lutidine, 1,8-diazabicyclo[5.4.0]undeca-7-ene (DBU), 1,5-diazabicyclo[4.3.0]nona-5-ene (DBN), 1,4-diazabicyclo[2.2.2]octene (DABCO), triethylamine, diisopropylethylamine, diisopropylpentylamine, and trimethylamine; and inorganic bases, such as lithium hydride, sodium hydride, potassium hydride, lithium hydroxide, sodium hydroxide, potassium hydroxide, lithium carbonate, sodium carbonate, potassium carbonate, cesium carbonate, sodium hydrogencarbonate, and potassium hydrogencarbonate. The reaction temperature in this step varies depending on the materials and the solvent to be used, but is generally from −20° C. to 100° C. and the reaction time is generally from ten minutes to two days.

Step 2: Compound (4) and Compound (5) are reacted in the presence of base in a solvent to produce Compound (6). In this step, although the amount of Compound (5) is not particularly limited, for example, from 1.2 to 1.8 Compound (4) equivalents may be used for reaction. Although the amount of the base is not particularly limited, for example, from 1.2 to 1.8 Compound (4) equivalents may be used for reaction. Although the solvent used in this step is not particularly limited as long as the solvent does not inhibit the reaction, examples of the solvent include: amides, such as N,N-dimethylformamide and N,N-dimethylacetamide; ethers, such as diethyl ether, diisopropyl ether, tetrahydrofuran, dioxane, and ethylene glycol dimethyl ether; halogenated hydrocarbons, such as dichloromethane and 1,2-dichloromethane; and the like. Examples of the base to be used include, but not particularly limited to: organic bases, such as pyridine, 4-dimethylaminopyridine (DMAP), collidine, lutidine, 1,8-diazabicyclo[5.4.0]undeca-7-ene (DBU), 1,5-diazabicyclo[4.3.0]nona-5-ene (DBN), 1,4-diazabicyclo[2.2.2]octene (DABCO), triethylamine, diisopropylethylamine, diisopropylpentylamine, and trimethylamine; and inorganic bases, such as lithium hydride, sodium hydride, potassium hydride, lithium hydroxide, sodium hydroxide, potassium hydroxide, lithium carbonate, sodium carbonate, potassium carbonate, cesium carbonate, sodium hydrogencarbonate, and potassium hydrogencarbonate. The reaction temperature in this step varies depending on the materials and the solvent to be used, but is generally from 0° C. to 100° C. and the reaction time is generally from 30 minutes to 24 hours.

Step 3: Deprotection of the protecting group $P^1$ for Compound (6) allows production of Compound (7). The method and the conditions for deprotection vary depending on the kind of the protecting group $P^1$. For example, it is possible to deprotect benzyl groups and benzyloxycarbonyl groups by catalytic hydrogenation and to deprotect tert-butoxycarbonyl groups by acid by a method with reference to generally used methods in organic chemistry (Protective Groups in Organic Synthesis Third Edition, John Wiley & Sons, Inc.).

Step 4: Compound (7) and Aldehyde Compound (8) are subjected to reductive amination reaction in the presence of a reducing agent in a solvent to produce Compound (1a). In this step, although the amount of Compound (8) is not particularly limited, for example, from 1.0 to 1.5 Compound (7) equivalents may be used for reaction. Although the amount of the reducing agent is not particularly limited, for example, from 2.0 to 4.0 Compound (7) equivalents may be used for reaction. Although the solvent used in this step is not particularly limited as long as the solvent does not inhibit the reaction, examples of the solvent include: amides, such as N,N-dimethylformamide and N,N-dimethylacetamide; ethers, such as diethyl ether, diisopropyl ether, tetrahydrofuran, dioxane, and ethylene glycol dimethyl ether; halogenated hydrocarbons, such as dichloromethane and 1,2-dichloromethane; and the like. Examples of the reducing agent include sodium borohydride, sodium cyanoborohydride, sodium triacetoxyborohydride, and the like. In addition, for the purpose of promoting formation of imine and accelerating the reaction, organic acid, such as acetic acid, may be used for pH adjustment. Moreover, organic base, such as pyridine, triethylamine, diisopropylethylamine, diisopropylpentylamine, and trimethylamine, may be used in the reaction. The reaction temperature in this step varies depending on the materials and the solvent to be used, but is generally from −20° C. to 100° C. and the reaction time is generally from ten minutes to two days.

Compound (7) and Carboxylic Acid Compound (9) are reacted using a condensing agent in a solvent to produce Compound (1a). It should be noted that, in this step, base and a condensation accelerator may be used in addition to the condensing agent for the purpose of accelerating the reaction. In this step, although the amount of Compound (9) is not particularly limited, for example, from 1.0 to 1.5 Compound (7) equivalents may be used for reaction. Although the amount of the condensing agent is not particularly limited, for example, from 1.0 to 1.5 Compound (7) equivalents may be used for reaction. Although the amount of the base is not particularly limited, for example, from 2.0 to 2.5 Compound (7) equivalents may be used for reaction. Although the solvent used in this step is not particularly limited as long as the solvent does not inhibit the reaction, examples of the solvent include: amides, such as N,N-dimethylformamide and N,N-dimethylacetamide; ethers, such as diethyl ether, diisopropyl ether, tetrahydrofuran, dioxane, and ethylene glycol dimethyl ether; halogenated hydrocarbons, such as dichloromethane and 1,2-dichloroethane; acetic esters, such as methyl acetate and ethyl acetate; and the like. Examples of the condensing agent include, but not particularly limited to N,N'-dicyclohexylcarbodiimide (DCC), N,N'-diisopropylcarbodiimide (DIPCI), 1-ethyl-3-(3-dimethylaminopropyl)carbodiimide (WSCI), 1-ethyl-3-(3-dimethylaminopropyl)carbodiimide hydrochloride (WSC·HCl), and the like. Examples of the base to be used include, but not particularly limited to: organic bases, such as pyridine, 4-dimethylaminopyridine (DMAP), collidine, lutidine, 1,8-diazabicyclo[5.4.0]undeca-7-ene (DBU), 1,5-diazabicyclo[4.3.0]nona-5-ene (DBN), 1,4-diazabicyclo[2.2.2]octene (DABCO), triethylamine, diisopropylethylamine, diisopropylpentylamine, and trimethylamine; and inorganic bases, such as lithium hydride, sodium hydride, potassium hydride, lithium hydroxide, sodium hydroxide, potassium hydroxide, lithium carbonate, sodium carbonate, potassium carbonate, cesium carbonate, sodium hydrogencarbonate, and potassium hydrogencarbonate. Examples of the condensation accelerator include, but not particularly limited to 4-dimethylaminopyridine (DMAP), 1-hydroxy-7-azobenzotriazole (HOAt), 1-hydroxybenzotriazole (HOBt), 3-hydroxy-3,4-dihydro-4-oxo-1,2,3-benzotriazole (HODhbt), N-hydroxy-5-norbornene-2,3-dicarboxyimide (HONB), pentafluorophenol (HOPfp), N-hydroxyphthalimide (HOPht), N-hydroxysuccinimide (HOSu), and the like. The reaction temperature in this step varies depending on the materials and the solvent to be used, but is generally from 0° C. to 100° C. and the reaction time is generally from 30 minutes to 24 hours.

Method B: Production Intermediate (4) May Also be Produced by the Method Represented by Reaction Scheme 2 Below.

[Reaction Scheme 2]

[Chem. 6]

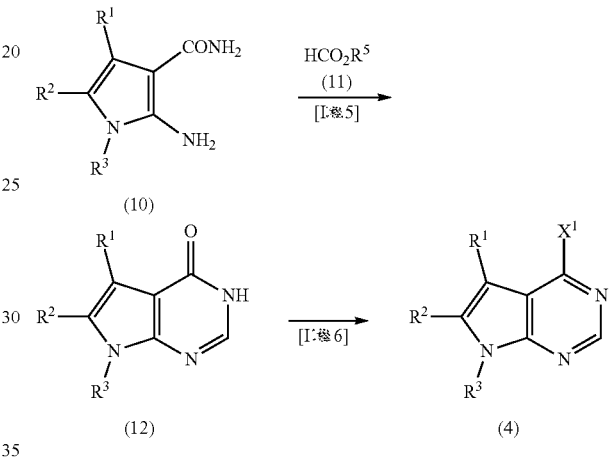

[where $R^1$, $R^2$, and $R^4$ denote the same definitions as above, $R^3$ denotes a $C_{3-6}$ cycloalkyl group, a $C_{6-10}$ aryl group optionally substituted by a halogen atom, or a ($C_{6-10}$ aryl) $C_{1-6}$ alkyl group, $R^5$ denotes a $C_{1-6}$ alkyl group, and $X^1$ denotes a leaving group, such as a halogen atom.]

Step 5: Compound (10) and Compound (11) are reacted in the presence of base in a solvent to produce Compound (12). Although the solvent used in this step is not particularly limited as long as the solvent does not inhibit the reaction, examples of the solvent include: amides, such as N,N-dimethylformamide and N,N-dimethylacetamide; ethers, such as diethyl ether, diisopropyl ether, tetrahydrofuran, dioxane, and ethylene glycol dimethyl ether; halogenated hydrocarbons, such as dichloromethane and 1,2-dichloroethane; alcohols, such as methanol and ethanol; and the like. Examples of the base to be used include, but not particularly limited to: organic bases, such as pyridine, 4-dimethylaminopyridine (DMAP), collidine, lutidine, 1,8-diazabicyclo[5.4.0]undeca-7-ene (DBU), 1,5-diazabicyclo[4.3.0]nona-5-ene (DBN), 1,4-diazabicyclo[2.2.2]octene (DABCO), triethylamine, diisopropylethylamine, diisopropylpentylamine, and trimethylamine; and inorganic bases, such as lithium hydride, sodium hydride, potassium hydride, lithium hydroxide, sodium hydroxide, potassium hydroxide, lithium carbonate, sodium carbonate, potassium carbonate, cesium carbonate, sodium hydrogencarbonate, and potassium hydrogencarbonate; metal alcoholates, such as sodium methoxide, sodium ethoxide, potassium methoxide, and potassium ethoxide. The reaction temperature in this step varies depending on the materials and the solvent to be used, but is generally from 0° C. to 120° C. and the reaction time is generally from 30 minutes to 24 hours.

The intermediates and products obtained by each reaction above may be subjected to purification process commonly used in organic synthetic chemistry, such as filtration, extraction, washing, drying, concentration, recrystallization, and various kinds of chromatography, for isolation and purification as needed. The intermediates may be provided without particular purification to later reaction.

It is possible to isolate various isomers by applying ordinary methods using differences in physicochemical properties among the isomers. For example, a racemic mixture can be led to an optically pure isomer by general racemic resolution process, such as a method including leading to a diastereomeric salt with general optically active acid, for example tartaric acid, for optical resolution and a method using optically active column chromatography. Such a diastereomeric mixture may be resolved by, for example, fractional crystallization, various kinds of chromatography, or the like. It is also possible to produce such an optically active compound using appropriate optically active materials.

(1) Acquisition and Preparation of Compounds

Compound A (2-[4-{(7-benzyl-5,6-dimethyl-7H-pyrrolo[2,3-d]pyrimidin-4-yl)oxy}piperidin-1-yl]-N(cyclopropylmethyl)acetamide) is a known material represented by a molecular formula $C_{26}H_{33}N_5O_2$ with a molecular weight of 447.57 and is an appropriately available material. For example, it is available by purchasing a product (ADM 12880492) sold by Asinex Japan Inc. It is also available by purchasing (K11.321.100) from Aurora Fine Chemicals. It is also possible to be prepared by a technique known by those skilled in the art, such as synthesis from a precursor compound 2-[4-{(7-benzyl-5,6-dimethyl-7H-pyrrolo[2,3-d]pyrimidin-4-yl)oxy}piperidin-1-yl]acetate (also available for purchase as ADM12880482 by Asinex Japan Inc., K11.321.097 by Aurora Fine Chemicals) and 1-cyclopropylmethanamine. Compound A is represented by the following structural formula.

[Chem. 7]

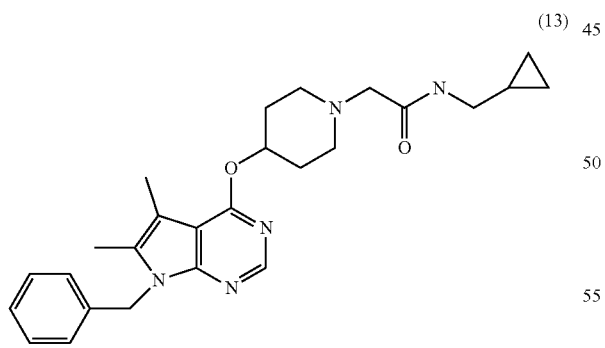

(13)

Instead of Compound A, an analogous compound represented by the formula (1) or (1') may be prepared for use. A representative example of the analogous compound to Compound A includes Compound A'. Compound A' (2-[4-{(7-cyclohexyl-5,6-dimethyl-7H-pyrrolo[2,3-d]pyrimidin-4-yl)oxy}piperidin-1-yl]-N(cyclopropylmethyl)acetamide) is a known material represented by a molecular formula $C_{25}H_{40}N_5O_2$ with a molecular weight of 439.6 and is an appropriately available material. For example, it is possible to purchase (K11.321.120) from Aurora Fine Chemicals. Compound A' is represented by the following structural formula.

[Chem. 8]

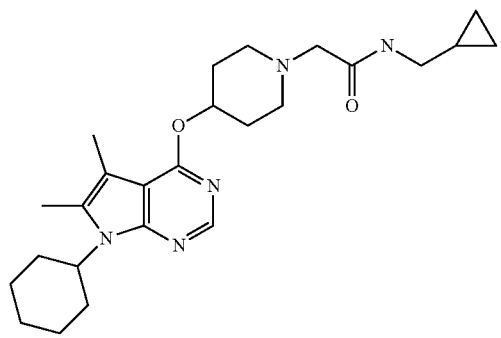

(14)

Compound B (3-[4-{(7-cyclopentyl-5,6-dimethyl-7H-pyrrolo[2,3-d]pyrimidin-4-yl)oxy}piperidin-1-yl]propanenitrile) is a known material represented by a molecular formula $C_{21}H_{29}N_5O$ with a molecular weight of 367.49 and is an appropriately available material. For example, it is available by purchasing a product (ADM 12880696) sold by Asinex Japan Inc. It is also available by purchasing (K11.321.154) from Aurora Fine Chemicals. It is also possible to be prepared by a technique known by those skilled in the art. Compound B is represented by the following structural formula.

[Chem. 9]

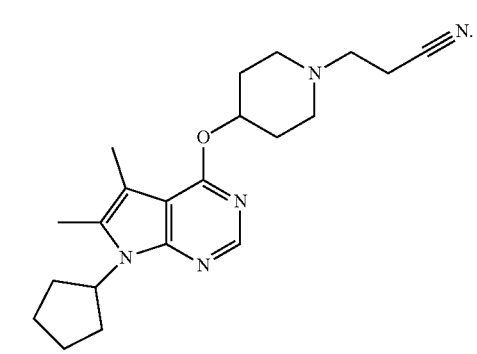

(15)

(2) Confirmation of Inflammatory Cytokine Production Inhibitory Effect

The effect of the prophylactic and/or therapeutic agent of the present invention can be confirmed by in vitro or in vivo experiments based on, for example, inhibition of production of IL-6, which is inflammatory cytokine, as an index. More specifically, the effect can be confirmed as, for example, an IL-6 production inhibitory effect of BAFF from THP-1 cells described later in Example 2. As another example, the effect can be confirmed as an IL-6 production inhibitory effect of BAFF from peripheral blood monocytes described later in Example 3. The effect is also appropriately confirmed by in vivo experiments using inflammatory disease model animals and the like.

(3) Confirmation of Autoantibody Production Inhibitory Effect

The effect of the prophylactic and/or therapeutic agent of the present invention can be confirmed by, for example, in vitro or in vivo experiments based on inhibition of IgG antibody production by B cells as an index. More specifically, the effect can be confirmed as, for example, an IgG antibody production inhibitory effect from B cells by coculture of BAFF-stimulated peripheral blood monocytes and the B cells described later in Example 4. As another example, the effect can be confirmed as an IgG production inhibitory effect by B cell-stimulation culture using peripheral blood mononuclear cells described later in Example 5. As still another example, the effect can be confirmed as an effect of inhibiting anti-dsDNA antibody production in the blood in systemic lupus erythematosus model mice described later in Examples 6 and 7. From these effects, it can be understood that the pyrrolopyrimidine compound in the formula (1) of the present invention represented by Compound A can be preferably used as a prophylactic and/or therapeutic agent for diseases exacerbated by excessive IgG production from B cells, such as inflammatory bowel disease and vasculitis (arteritis, etc.). Because the spontaneous IgG antibody production from B cells is inhibited (refer to Examples 4 and 5 described later for details) and the anti-dsDNA antibody production is inhibited (refer to Examples 6 and 7 described later for details), it is possible to reasonably understand that the pyrrolopyrimidine compound in the formula (1) of the present invention represented by Compound A is characterized by autoantibody production and can be used for prophylactic and therapeutic purposes against various autoimmune diseases associated with BAFF. Moreover, a therapeutic effect on autoimmune diseases can also be appropriately confirmed by in vivo experiments using autoimmune disease model animals and the like.

(4) Confirmation of Nephritis Inhibitory Effect

The effect of the prophylactic and/or therapeutic agent of the present invention can be confirmed by in vivo experiments based on inhibition of protein contents in the urine or inhibition of lymphocytic infiltration in kidney tissues as an index. More specifically, the effect can be confirmed as an effect of inhibiting protein contents in the urine in disease model mice that spontaneously develop glomerulonephritis (systemic lupus erythematosus model mice) described later in Example 8. The effect can also be confirmed as an effect of reducing lymphocytic infiltration in kidney tissues in disease model mice that spontaneously develop inflammatory diseases, such as nephritis, (systemic lupus erythematosus model mice) described later in Example 9. From these effects, it can be understood that the pyrrolopyrimidine compound in the formula (1) of the present invention represented by Compound A can be preferably used as a prophylactic and/or therapeutic agent for impaired renal function exacerbated by inflammatory renal disease, lupus nephritis, and the like.

(5) Confirmation of Inflammation Inhibitory Effect in Glandular Tissues

The effect of the prophylactic and/or therapeutic agent of the present invention can be confirmed by in vivo experiments based on reduction of lymphocytic infiltration in glandular tissues, such as lacrimal glands and submandibular glands, as an index. More specifically, the presence of an anti-inflammatory effect can be confirmed by reduction of lymphocytic infiltration in the lacrimal and submandibular gland tissues in disease model (systemic lupus erythematosus model) mice that spontaneously develop inflammatory diseases, such as nephritis, and develops multiple autoimmune phenomena described later in Example 9. From these effects, it can be understood that the pyrrolopyrimidine compound in the formula (1) of the present invention represented by Compound A can be preferably used as a prophylactic and/or therapeutic agent for inflammatory diseases occurring in the lacrimal glands, the submandibular glands, and the like.

(6) Preparation of Prophylactic and/or Therapeutic Agent for Inflammatory Diseases Containing Pyrrolopyrimidine Compound in Formula (1) of Present Invention, Such as Compound a, as Active Ingredient In the prophylactic and/or therapeutic agent for inflammatory diseases containing the pyrrolopyrimidine compound, as an active ingredient, in the formula (1) of the present invention, such as Compound A of the present invention, it is possible to use not only the pyrrolopyrimidine compound itself but also a compound in the form of a salt or solvate thereof as the pyrrolopyrimidine compound in the formula (1), such as Compound A, as an active ingredient. Such a compound in the form of a salt or solvate may be produced by ordinary methods. It is understood that even the case of being referred to simply as Compound A or the pyrrolopyrimidine compound of the present invention equally involves the invention in the case of using a compound in the form of a salt or solvate of Compound A or the pyrrolopyrimidine compound of the present invention.

Although the salt is not particularly limited as long as it is pharmaceutically acceptable, examples of the salt include: alkali metal salts, such as sodium salt and potassium salt; alkaline earth metal salts, such as calcium salt and magnesium salt; organic basic salts, such as ammonium salt and trialkylamine salt; mineral acid salts, such as hydrochloride and sulfate; organic acid salts, such as acetate; and the like.

Examples of the solvate include hydrates, alcoholates (e.g., ethanolate), and the like.

The route of administration of the prophylactic and/or therapeutic agent for inflammatory diseases containing the pyrrolopyrimidine compound, as an active ingredient, in the formula (1) of the present invention, such as Compound A of the present invention, is not particularly limited and the prophylactic and/or therapeutic agent may be an oral agent or a parenteral agent.

For example, the oral agent may be in dosage forms of tablets, capsules, granules, powders, syrups, and the like. The parenteral agent may be in dosage forms of injections, ophthalmic preparations, nasal preparations, ointments, creams, lotions, gel preparations, sprays, and the like. These pharmaceutical preparations may be produced by known methods. For example, in the case of pharmaceutical preparations for oral administration, the agent may be produced by formulating, in appropriate combination: solubilizers, such as gum tragacanth, gum Arabic, sucrose fatty acid ester, lecithin, olive oil, soybean oil, and PEG 400; diluents, such as starch, mannitol, and lactose; binders, such as methyl cellulose, sodium carboxymethyl cellulose, and hydroxypropyl cellulose; disintegrants, such as crystalline cellulose and calcium carboxymethyl cellulose; lubricants, such as talc and magnesium stearate; fluidity improvers, such as light anhydrous silicic acid; and the like. For example, in the case of pharmaceutical preparations for injection, the agent may be prepared by dissolving or diluting a dried product or a storage solution of the pyrrolopyrimidine compound in the formula (1) of the present invention, such as aseptically stored Compound A, with a physiological saline solution for intravenous injection or a buffer solution. To increase the solubility of the pyrrolopyrimidine compound in the formula (1) of the present invention, such as Compound A, known techniques are applicable as appropriate, such as changing the solvent, granulating Compound A into ultrafine particles, and including Compound A in cyclodextrins. It is possible to produce hypodermic, intramuscular, and intravenous injections using ordinary methods by adding a pH adjusting agent, a buffer, a stabilizer, an isotonizing agent, a local anesthetic, and the like together with the pyrrolopyrimidine compound in the formula (1) of the present invention, such as Compound A. Examples of the pH adjusting agent and the buffer include sodium citrate, sodium acetate, sodium phosphate, and the like. Examples of the stabilizer include sodium pyrosulfite, EDTA (sodium edetate), thioglycolic acid, thiolactic acid, and the like. Examples of the local anesthetic include procaine hydrochloride, lidocaine hydrochloride, and the like. Examples of the isotonizing agent include sodium chloride, grape sugar, and the like. Meanwhile, in the case of preparation for external use, such as ointments, creams, and lotions, the agent may be prepared by dissolving or dispersing the pyrrolopyrimidine compound in the formula (1) of the present invention, such as Compound A, in a lyophilic, water-soluble, or emulsion base material. In the case of preparation as an ointment, the base material for the ointment is selected from known or generally used ones and is preferably selected from, for example, higher fatty acids and esters thereof (e.g., adipic acid, myristic acid, palmitic acid, stearic acid, oleic acid, adipate, myristate, palmitate, hexyl laurate, ethyl isooctanoate, etc.), waxes (e.g., spermaceti wax, beeswax, diazepam, etc.), surfactants (e.g., polyoxyethylene alkyl ether phosphate, higher alcohols (e.g., cetanol, stearyl alcohol, cetostearyl alcohol, etc.), silicon oil (e.g., dimethylpolysiloxane, methylphenylpolysiloxane, glycol methylpolysiloxane, silicone glycol polymers, etc.), hydrocarbons (e.g., hydrophilic Vaseline, white petrolatum, purified lanoline, liquid paraffin, etc.), water, humectants (e.g., glycerin, propylene glycol, butylene glycol, sorbitol, etc.), anti-irritants, and other additives. The pyrrolopyrimidine compound in the formula (1) of the present invention, such as Compound A of the present invention, is appropriately formulated in combination with these base materials to produce pharmaceutical preparations for percutaneous and mucosal, such as oral mucosal, administration. Since the properties of good adhesion and less likelihood of being washed away by saliva and the like are expected for oral mucosal administration, it is desirable to increase the adhesiveness by adding celluloses, paraffin, and the like to a hydrophobic base material. Lotions are appropriately prepared similar to the ointments and prepared as liquid pharmaceutical preparations with low viscosity by increasing the water content. The base material to be used for creams is selected from various known or generally used base materials, and examples of the base material include higher fatty acid esters (e.g., diester of myristic acid, hexyl palmitate, diethyl sebacate, hexyl laurate, cetyl isooctanoate, etc.), lower alcohols (e.g., ethanol, isopropanol, etc.), hydrocarbons (e.g., liquid paraffin, squalene, etc.), polyhydric alcohols (e.g., propylene glycol, 1,3-butylene glycol, etc.), higher alcohols (e.g., 2-hexyldecanol, cetanol, 2-octyldecanol, etc.), emulsifiers (e.g., polyoxyethylene alkyl ethers, fatty acid esters, polyethylene glycol fatty acid ester, etc.), antiseptics (e.g., paraoxybenzoate), anti-irritants, and other additives. It is possible to obtain such a cream by adding the pyrrolopyrimidine compound in the formula (1) of the present invention, such as Compound A of the present invention, to any of the above base materials and further appropriately combining an ultraviolet absorber or an antioxidant as needed. In the case of preparing ophthalmic preparations, the ophthalmic preparations may be any of aqueous ophthalmic preparations, non-aqueous ophthalmic preparations, ophthalmic suspensions, ophthalmic emulsions, ophthalmic ointments, and the like. Such a pharmaceutical preparation may be produced as a composition suitable for the form of administration by (pharmaceutical preparation) methods known to those skilled in the art by combining pharmaceutically acceptable carriers as needed, particularly carriers acceptable for ophthalmic solutions, for example, isotonizing agents, chelating agents, stabilizers, pH adjusting agents, antiseptics, antioxidants, solubilizers, thickening agents, and the like. In the case of preparing the ophthalmic preparations, it may be done by, for example, dissolving or suspending the pyrrolopyrimidine compound in the formula (1) of the present invention, such as Compound A, in an aqueous solvent, such as sterile purified water and a physiological saline solution, or a non-aqueous solvent, such as vegetable oil including cottonseed oil, soybean oil, sesame oil, peanut oil, and the like, controlling the osmotic pressure at a predetermined level, and performing sterilization, such as filtration sterilization. As the aqueous base material for ophthalmic preparations, generally used additives are appropriately combined, such as an isotonizing agent, a buffer, and a preservative. Examples of the isotonizing agent include sodium chloride, potassium chloride, polyhydric alcohols, sugars, and the like, examples of the buffer include sodium borate, sodium citrate, sodium monohydrogen phosphate, sodium dihydrogen phosphate, and the like, and examples of the preservative include benzethonium hydrochloride, benzalkonium hydrochloride, chlorobutanol, and the like. In addition, stabilizers, such as glycerin and polysorbate 80, pH adjusters, and the like are combined as needed. It should be noted that in the case of preparing such an ophthalmic ointment, it is possible to contain a base material for the ointment in addition to the above various components. Preferred examples of the base material for the ointment include, but not particularly limited to: oily base materials, such as Vaseline, liquid paraffin, and polyethylene; emulsion base materials produced by emulsifying oil and aqueous phases with a surfactant and the like; water-soluble base materials of hydroxypropylmethyl cellulose, carboxymethyl cellulose, polyethylene glycol, and the like; and the like. In the case of preparing gel preparations, the gel base material is selected from various known or generally used base materials, and examples of the base material include lower alcohols (e.g., ethanol, isopropyl alcohols, water, gelling agents (e.g., carboxyvinyl polymers, hydroxyethyl cellulose, ethyl cellulose, carboxyethyl cellulose, polypropylene glycol alginate, etc.), neutralizers (e.g., triethanolamine, diisopropanolamine, sodium hydroxide, etc.), surfactants (e.g., sorbitan sesquioleate, sorbitan trioleate, sorbitan monooleate, sorbitan monostearate, sorbitan monolaurate, polyethylene glycol monostearate, polyoxyethylene phenyl ether, polyoxyethylene lauryl ether, etc.), anti-irritants, and other additives. Compound A of the present invention is appropriately formulated in combination with these base materials to produce pharmaceutical preparations for percutaneous and mucosal, such as oral mucosal, administration. Nasal preparations and sprays are prepared as liquid pharmaceutical preparations containing the pyrrolopyrimidine compound in the formula (1) of the present invention, such as Compound A. Such a nasal preparation is desirably contained in a container in a shape suitable for application (dropping) in the nasal cavity. Such a spray is prepared in the form of being stored in a spray container containing a propellant together with the liquid pharmaceutical preparation. As the propellant, gas, such as carbon dioxide, is used. The spray may be applied not only to the epidermis but also into the nasal cavity and the oral cavity, and a spray container in a shape suitable for usage is appropriately selected and used for preparation.

(7) Applications of Prophylactic and/or Therapeutic Agent for Inflammatory Diseases Containing Pyrrolopyrimidine Compound, as Active Ingredient, in Formula (1) of Present Invention, Such as Compound A As described later in Examples, in the prophylactic and/or therapeutic agent for inflammatory diseases containing the pyrrolopyrimidine compound, as an active ingredient, in the formula (1) of the present invention, such as Compound A, the pyrrolopyrimidine compound in the formula (1) of the present invention, such as Compound A of the present invention, has inhibitory action on biological effects (IgG production, IL-6 production) led by BAFF in human peripheral cells (B cells, monocytes). In addition, as described later in Examples, the pyrrolopyrimidine compound in the formula (1) of the present invention, such as Compound A of the present invention, has inhibitory action on production of autoantibodies in vivo (specific examples include anti-dsDNA antibodies) and inhibitory action on inflammatory response of biological tissues (specific examples include lymphocyte infiltration into tissues). Such a pharmacological action indicates that the pyrrolopyrimidine compound in the formula (1) of the present invention, such as Compound A of the present invention, is useful for prophylactic and therapeutic purposes against inflammatory diseases, particularly autoimmune diseases characterized by autoantibody production, and among others, Sjögren syndrome and systemic lupus erythematosus. This compound is also preferably used as a prophylactic and/or therapeutic agent for diseases exacerbated by excessive IgG production from B cells, such as inflammatory bowel disease and vasculitis (arteritis, etc.). In addition, diseases exhibiting enhanced or abnormal immune function related to activated B cells are also intended for prophylactic or therapeutic targets of the present invention. Examples of these diseases are as follows: dermatomyositis, polymyositis, atopic dermatitis, eczema, bronchial asthma, scleroderma, IgG4 related disease, primary biliary cirrhosis, primary sclerosing cholangitis, discoid lupus erythematosus, morphea, mixed connective tissue disease, rapidly progressive glomerulonephritis, pemphigus, pemphigoid, myasthenia gravis, idiopathic thrombocytopenic purpura, hyperthyroidism, chronic thyroiditis, antiphospholipid antibody syndrome, autoimmune gastritis, Goodpasture syndrome, pernicious anemia, and autoimmune hemolytic anemia.

(8) Form of Administration of Prophylactic and/or Therapeutic Agent for Inflammatory Diseases Containing Pyrrolopyrimidine Compound, as Active Ingredient, in Formula (1) of Present Invention, Such as Compound A The effective dose of the pyrrolopyrimidine compound in the formula (1) of the present invention, such as Compound A, as an active ingredient of the prophylactic and/or therapeutic agent for inflammatory diseases of the present invention appropriately varies depending on various aspects, such as the condition of the patient and the symptoms. The dose per day of the pyrrolopyrimidine compound in the formula (1) of the present invention, such as Compound A, in the case of oral administration may be administered once a day or several times by dividing the dose. On the contrary, the frequency of administration may be reduced to once a two or more days by administering the dose for several days in one time. Similarly, the dose of the pyrrolopyrimidine compound in the formula (1) of the present invention, such as Compound A, in the case of systemic administration as an injection may be administered once a day or several times by dividing the dose. On the contrary, the frequency of administration may be reduced to once a two or more days by injecting the dose for several days in one time. The agent may also be continuously administered by intravenous drip and the like. In the case of locally administering a parenteral agent, such as an ophthalmic preparation, a nasal preparation, an ointment, a lotion, a cream, a gel preparation, and a spray, it is possible to appropriately adjust the combined amount of the pyrrolopyrimidine compound in the formula (1) of the present invention, such as Compound A, in the pharmaceutical composition as medicine for external application, the frequency of local administration, the application area, and the like. In any case, administration does not have to be continuous or periodic and may be appropriately performed at intervals in accordance with changes in symptoms and the like. When single dose administration results in cure or remission, multiple dose administration does not have to be performed. The administration may be resumed in the case of recurrence or exacerbation of symptoms.

The route of administration of the prophylactic and/or therapeutic agent for inflammatory diseases containing the pyrrolopyrimidine compound, as an active ingredient, in the formula (1) of the present invention, such as Compound A of the present invention, is not particularly limited. In the case of SS as a typical exemplification of a therapeutic target, dryness of the eyes (dryeyes), dryness of the mouth, and dryness of the nasal cavity are marked symptoms and the sicca symptoms of the skin and the vagina are also known, and thus any of the parenterally administered pharmaceutical preparations for local administration are preferably used, such as ophthalmic preparations, nasal preparations, ointments, creams, lotions, and gel preparations. Sprays particularly prepared for administration in the nasal cavity and the oral cavity may also be used.

The administration period may be appropriately controlled in accordance with the patient's condition. While the administered dose during the administration period may be appropriately controlled, the form of administration is exemplified by continuous administration of a fixed amount or relatively high dose administration only in an initial period of administration shifted to constant administration of a maintenance dose in a less amount.

(9) Applications [1] of Pyrrolopyrimidine Compound in Formula (1) of Present Invention, Such as Compound A As described later in Examples 2 and 3, the pyrrolopyrimidine compound in the formula (1) of the present invention, such as Compound A, inhibits inflammatory cytokine IL-6 production that is led in monocytes stimulated with BAFF. It is thus possible to use the compound for the method of inhibiting inflammatory cytokine production, including administering the pyrrolopyrimidine compound in the formula (1) of the present invention, such as Compound A. In this context, representative inflammatory cytokine is IL-6, and IL-6 production can be quantitatively confirmed by ELISA using anti-IL-6 antibodies and the like. By focusing on inhibition of the amounts of IL-6 production, it is also possible to screen a compound that is effective for prophylactic and therapeutic purposes against inflammatory diseases using Compound A as a positive control.

(10) Applications [2] of Pyrrolopyrimidine Compound in Formula (1) of Present Invention, Such as Compound A As described later in Examples 4 and 5, the pyrrolopyrimidine compound in the formula (1) of the present invention, such as Compound A, inhibits IgG antibody production that is led in B cells stimulated with BAFF. It is thus possible to use the compound for the method of inhibiting IgG antibody production by activated B cells, including administering the pyrrolopyrimidine compound in the formula (1) of the present invention, such as Compound A. In this context, IgG antibody production can be quantitatively confirmed by ELISA using anti-IgG antibodies and the like. By focusing on inhibition of the amounts of IgG antibody production, it is also possible to screen a compound that is effective for prophylactic and therapeutic purposes against autoimmune diseases and diseases exacerbated by excessive IgG production using Compound A as a positive control.

EXAMPLES

The present invention will be more specifically described below by way of Examples while the present invention is not at all limited to these Examples.

Example 1 Screening of Compound

Materials and Method

In 24-well plates (manufactured by Corning Inc.) in a RPMI-1640 culture medium (produced by ATCC) containing 10% fetal bovine serum (produced by JRH Biosciences), $5 \times 10^5$ cells of human monocytic leukemia cell line THP-1 (obtained from a bioresource bank, Japanese Collection of Research Bioresource) were seeded per well. IFNγ (interferon γ, produced by BD Pharmingen) was added to a final concentration of 200 ng/mL and cultured in a 5% $CO_2$ environment at 37° C. After four days of culture, the culture broth in each well was removed and the cells were washed twice with the culture medium, followed by addition of the culture medium containing a final concentration of 2 μg/mL of recombinant human soluble BAFF (produced by Chemicon), and respective test compounds were added to a final concentration of 20 μM or 2 μM to continue the culture in the same conditions. After three days of culture, the culture supernatant was collected to determine the IL-6 content in the supernatant by ELISA. For ELISA, mouse anti-human IL-6 antibody (produced by BD Pharmingen), biotin-labeled anti-human IL-6 antibody (produced by BD Pharmingen), and HRP-labeled streptavidin (produced by BD Pharmingen) were used. The test compound groups were used by purchasing from Asinex. In the test system, Compound 27 (BIK-13) in PTL 1 was used as a positive control (compound with inhibitory action on IL-6 production by monocytic cells). BIK-13 was the same as the compound of ADM 12880656 by Asinex Japan Inc.

Results

Each test compound was evaluated based on the IL-6 production inhibitory effect as an index, resulting in finding 2-[4-{(7-benzyl-5,6-dimethyl-7H-pyrrolo[2,3-d]pyrimidin-4-yl)oxy}piperidin-1-yl]-N(cyclopropylmethyl)acetamide with a structure (13) below (Compound A) and 3-[4-{(7-cyclopentyl-5,6-dimethyl-7H-pyrrolo[2,3-d]pyrimidin-4-yl)oxy}piperidin-1-yl]propanenitrile with a structure (15) below (Compound B).

[Chem. 7]

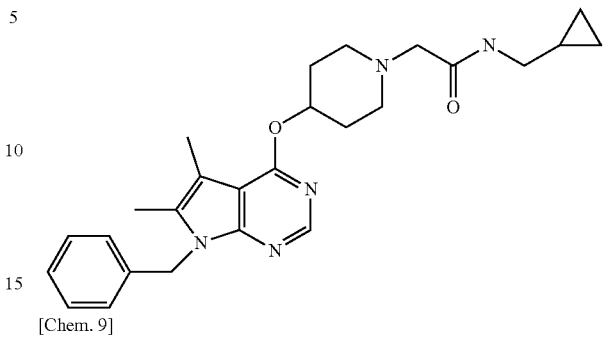

[Chem. 9]

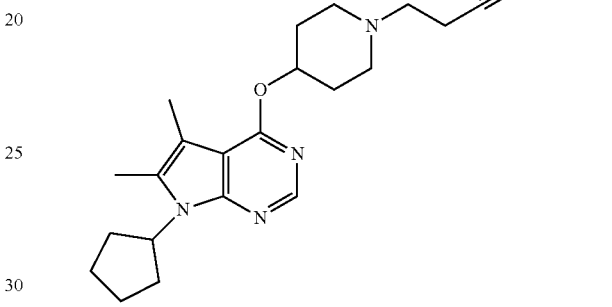

Example 2 IL-6 Production Inhibitory Effect of BAFF

Materials and Method

In the presence of 200 ng/mL recombinant human IFNγ (same as Example 1) (entire culture scale of 24-well culture plates at 2 mL/well), $5 \times 10^5$ cells of human monocytic cell line THP-1 (same as Example 1) were cultured using a 10% FBS/RPMI 1640 culture medium in a 5% $CO_2$ environment at 37° C. for four days (96 hours). Four days later, an operation of removing the supernatant, adding a new medium, leaving it still in an incubator, and removing the supernatant was repeated twice. After removing the supernatant, recombinant human BAFF (2 μg/mL) was dissolved together with Compound A (ADM 12880492, Asinex Japan Inc.) or Compound B (ADM 12880696, Asinex Japan Inc.) in a medium and added to the culture wells to be cultured for three days. Three days later, the culture supernatant was collected to determine the IL-6 content in the culture supernatant by IL-6 specific ELISA. As a control, instead of Compound A or Compound B, BIK-13 was used.

Results

The results are illustrated in FIG. 1A (the case of using Compound A), FIG. 1B (the case of using Compound B), and FIG. 1C (the case of using BIK-13).

When Compound A or Compound B was added (0.04 μM, 0.2 μM, and 1 μM) together with human BAFF, significant (p<0.001) IL-6 production inhibitory effects were found at any concentration compared with the control (FIGS. 1A and 1B).

In contrast, when BIK-13 was added (1.2 μM, 6 μM, and 30 μM), significant (p<0.001) IL-6 production inhibitory effects were found compared with the case of adding no compound (adding human BAFF only) in the case of adding 6 μM and 30 μM while no significant difference was found compared with the case of adding no compound (adding human BAFF only) in the case of adding 1.2 μM (FIG. 1C).

While Compound A exhibited an inhibitory effect on the amount of IL-6 production far below 50% (25±1.42%) the relative amount of production even in the case of added at the lowest concentration of 0.04 μM, BIK-13 did not inhibit down to 50% (52.8±2.2%) the relative amount of production even in the case of added at the highest concentration of 30 μM (FIGS. 1A and 1C). These results are considered that Compound A in the system of Example 2 using the human monocytic cell line exhibited a stronger IL-6 production inhibitory effect at least 750 times or more than BIK-13. While Compound B exhibited an inhibitory effect on the amount of IL-6 production below 50% the relative amount of production in the case of added at the concentration of 30 μM, BIK-13 did not inhibit down to 50% the relative amount of production even in the case of added at the concentration of 30 μM (FIGS. 1B and 1C). These results are considered that Compound B in the system of Example 2 using the human monocytic cell line exhibited a stronger IL-6 production inhibitory effect than BIK-13.

Example 3 IL-6 Production Inhibitory Effect of BAFF from Human Peripheral Blood Monocytes Materials and Method Monocytes were isolated from normal healthy human peripheral blood using CD14-microbeads. In the presence of 2 μg/mL recombinant human BAFF (same as Example 2) and Compound A (2 μM and 10 μM) (entire culture scale of 24-well culture plates at 2 mL/well), 5×10$^5$ of the isolated monocytes were cultured using a 10% FBS/RPMI 1640 culture medium in a 5% CO$_2$ environment at 37° C. for four days. Four days later, the supernatant was removed to determine the IL-6 content in the culture supernatant by IL-6 specific ELISA. For comparison, experiments using BIK-13 instead of Compound A were also performed.

Results

The results are illustrated in FIG. 2.

When Compound A was added (2 μM and 10 μM) together with human BAFF, significant (p<0.001) IL-6 production inhibitory effects were found at any concentration compared with the control of adding no compound (adding human BAFF only) (center in FIG. 2).

In contrast, when BIK-13 was added, a significant (p<0.05) IL-6 production inhibitory effect was found compared with the control in the case of adding 10 μM while no significant difference was found in the case of adding 2 μM (right in FIG. 2).

In addition, the relative amount of production by adding 2 μM of Compound A was 66.4±0.283% while the relative amount of production by adding 10 μM of BIK-13 was 80.2±14.5%, and it can be understood that stronger inhibition occurred in the former case than the latter case.

These results are considered that Compound A in the system of Example 3 using the human peripheral blood monocytes of normal healthy individuals exhibited a stronger IL-6 production inhibitory effect at least 5 times or more than BIK-13.

Example 4 Inhibitory Effect on IgG Production from BAFF-Stimulated Peripheral Blood Monocytes and Cocultured B Cells Materials and Method Monocytes were isolated from Sjögren syndrome patient peripheral blood using CD14 microbeads, and B cells were isolated from the peripheral blood using CD19 microbeads. Using Transwell® culture plates, 2×10$^5$ monocytes per well were seeded in the upper plate and 1×10$^5$ B cells in the lower plate to be cultured in the presence of 2 μg/mL recombinant human BAFF (same as Example 2) and Compound A (1 μM and 10 μM) using a 10% FBS/RPMI 1640 culture medium in a 5% CO$_2$ environment at 37° C. for four days (coculture of the peripheral blood monocytes and the B cells via a membrane). Four days later, the supernatant was removed and the culture supernatant was collected to determine the IgG content in the culture supernatant by ELISA. As controls, experiments in the case of not adding Compound A and the case of adding neither Compound A nor BAFF were also performed. Moreover, for comparison with the effects of Compound A, experiments using BIK-13 instead of Compound A were also performed.

Results

The results are illustrated in FIG. 3.

When Compound A was added (1 μM and 10 μM) together with human BAFF, significant (p<0.01 or p<0.001) IgG antibody production inhibitory effects were found at any concentration compared with the control of adding no Compound A (B+mono+BAFF in FIG. 3) (left in FIG. 3). The IgG antibody production level in the case of adding 10 μM of Compound A was lower than the level in the case of adding none (adding neither Compound A nor BAFF; none in FIG. 3). This can be understood that the effect of IgG antibody production enhancement by BAFF was completely cancelled and further the IgG antibody production was inhibited below the basal level.

In contrast, when BIK-13 was added, a significant (p<0.01) IL-6 production inhibitory effect was found compared with the control in the case of adding 10 μM while no significant difference was found in the case of adding 1 μM (right in FIG. 3). While significant inhibition was found when adding 10 μM of BIK-13, it is recognized that the effect of IgG antibody production enhancement by BAFF was not completely cancelled different from the case of adding 10 μM of Compound A (right in FIG. 3).

These results are considered that Compound A in the system of Example 4 using coculture of BAFF-stimulated peripheral blood monocytes and B cells exhibited a stronger inhibitory effect on IgG antibody production approximately 10 times than BIK-13.

Example 5 Inhibitory Effect on IgG Production by B Cell-Stimulation Culture Using Peripheral Blood Mononuclear Cells (PBMC)

Materials and Method

Peripheral blood mononuclear cells were isolated from normal healthy human peripheral blood by density gradient centrifugation using Ficoll. In the presence of 5 μg/mL anti-human IgM antibody, 1 μg/mL anti-human CD40 antibody, 30 ng/mL recombinant human IL-21, 30 ng/mL recombinant human BAFF, and Compound A (0.4 μM, 2

μM, and 10 μM), $2\times10^5$ peripheral blood mononuclear cells were cultured using a 10% FBS/RPMI 1640 culture medium in a 5% $CO_2$ environment at 37° C. for seven days. The cells were cultured in 96-well round-bottom culture plates in a scale of 200 μL per well. Seven days later, the supernatant was removed and the culture supernatant was collected to determine the IgG content in the culture supernatant by ELISA. As controls, experiments in the case of not adding Compound A and the case of adding neither Compound A nor BAFF were also performed. Moreover, for comparison with the effects of Compound A, experiments using BIK-13 instead of Compound A were also performed.

Results

The results are illustrated in FIG. 4.

When Compound A was added (0.4 μM, 2 μM, and 10 μM) together with human BAFF, significant (respectively, $p<0.05$, $p<0.01$, and $p<0.001$) IgG antibody production inhibitory effects were found at any concentration compared with the control of adding no Compound A (control in FIG. 4) (FIG. 4). The IgG antibody production level in the case of adding 10 μM of Compound A was at the same level as in the case of adding none (adding neither Compound A nor BAFF; none in FIG. 4), and it can be understood that the effect of IgG antibody production enhancement by BAFF was almost completely cancelled.

In contrast, when BIK-13 was added, a significant ($p<0.01$) IL-6 production inhibitory effect was found compared with the control in the case of adding 10 μM while no significant difference was found in the case of adding 0.4 μM and 2 μM (the results of the experiments using BIK-13 are not shown).

These results are considered that Compound A in the system of Example 5 performing B cell-stimulation culture using PBMC exhibited a stronger inhibitory effect on IgG antibody production approximately 25 times than BIK-13.

Example 6 Effect (1) of Inhibiting Anti-dsDNA Antibody Production in Blood Using Inflammatory Disease Model Mice Developing Autoimmune Phenomena Materials and Method MRL/lpr mice (purchased from Charles River Laboratories Japan, Inc.) were used as disease model (may also be referred to as collagen disease model or systemic lupus erythematosus (SLE) model) mice developing inflammatory diseases at a high rate and developing multiple autoimmune phenomena. Approximately 80% or more of the MRL/lpr mice develop systemic vasculitis around four to five months old. In addition, it is also known that the same individual spontaneously develops, not only vasculitis, but also glomerulonephritis, arthritis, sialadenitis, and the like (J. Jpn. Coll. Angiol., 2009, 49 11-16.).

Experiments were performed as follows:
Group 1: administered a physiological saline solution only (saline);
Group 2: administered 0.04 mg/kg of Compound A;
Group 3: administered 0.2 mg/kg of Compound A;
Group 4: administered 1 mg/kg of Compound A.

Nine-week-old MRL/lpr mice (female) were classified into four groups (five individuals per group) and predetermined administration was initiated (0 w) on the individuals in each group.

The administration was performed five times a week for 16 weeks by intravenous injection.

The blood was collected over time (0 w, 4 w, 8 w, 12 w, and 16 w) measure the anti-dsDNA antibody titers in the blood. The anti-dsDNA antibody is a kind of antinuclear antibody and is known to be frequently and specifically detected in the serum of SLE patients.

The anti-dsDNA antibody titers in the blood were measured with "LBIS™ anti-dsDNA mice ELISA KIT" (AKRDO-061, produced by Fujifilm Corp.). The specific procedure was as follows:

1) washing an immobilized antigen 96-well plate in the kit three times with a washing buffer provided in the kit;
2) adding 100 μL/well diluted sample MRL or standard anti-mouse dsDNA antibody solution and leaving it still at room temperature for two hours;
3) after washing the plate three times with the washing buffer, adding 100 μL/well labeled antibody (peroxidase conjugated anti-mouse IgG antibody) and leaving it still at room temperature for two hours;
4) after washing the plate three times with the washing buffer, adding 100 μL/well chromogenic reagent (TMB solution) and leaving it still at room temperature for 20 minutes to generate color; and
5) adding 100 μL/well reaction terminator (1M $H_2SO_4$) to terminate the reaction and measure $OD_{450}$ nm.

Results

The results are illustrated in FIG. 5.

When Compound A was added (0.04 mg/kg, 0.2 mg/kg, and 1 mg/kg), a tendency of decrease in the anti-dsDNA antibody titers in the blood was found at any dose in 8 w or later compared with the control of adding no Compound A (saline in FIG. 5). In the 16th week, when Compound A was administered at 0.2 mg/kg and 1 mg/kg, significant (respectively, $p<0.05$) anti-dsDNA antibody titer inhibitory effects were found compared with the control (FIG. 5).

Example 7 Effect (2) of Inhibiting Anti-dsDNA Antibody Production in Blood Using Inflammatory Disease Model Mice Developing Autoimmune Phenomena Materials and Method NZB/WF1 mice (purchased from Japan SLC, Inc.) were used as disease model (may also be referred to as systemic lupus erythematosus (SLE) model) mice producing anti-dsDNA antibodies with age and spontaneously developing glomerulonephritis. Except for the following exceptions, present Example was performed by the same materials and method as Example 6 above.

Experiments were performed as follows:
Group 1: administered a physiological saline solution only (saline);
Group 2: administered 0.2 mg/kg of Compound A;
Group 3: administered 1 mg/kg of Compound A.

NZB/WF1 mice (female) of 20 weeks old were classified into the above three groups (five individuals per group) and predetermined administration was initiated (0 w) on the individuals in each group.

The administration was performed five times a week for 20 weeks by intravenous injection.

Results

The results are illustrated in FIG. 6.

When Compound A was added (0.2 mg/kg and 1 mg/kg), a tendency of decrease in the anti-dsDNA antibody titers in the blood was found at any dose in 12 w or later compared with the control of adding no Compound A (saline in FIG. 6). In the 12th and 16th weeks, when Compound A was administered at 1 mg/kg, significant (respectively, $p<0.05$) anti-dsDNA antibody titer inhibitory effects were found compared with the control (FIG. 6).

From the results of inhibiting anti-dsDNA antibody production in the blood described in Examples 6 and 7, it was confirmed that Compound A exhibits excellent pharmacological action in vivo as well in prophylactic and therapeutic applications to inflammatory diseases, particularly autoimmune diseases.

Example 8 Urine Protein Inhibitory Effect Using Inflammatory Disease Model Mice Developing Autoimmune Phenomena Materials and Method Present Example was performed simultaneously with Example 7 using NZB/WF1 mice. Except for the following exceptions, present Example was performed by the same materials and method as Example 7 above.

Experiments were performed as follows.

The urine was collected over time (0 w, 4 w, 7 w, 12 w, 16 w, and 18 w) to evaluate the protein content in the blood in the urine using urine protein test strips. It is known that SLE patients are prone to develop lupus nephritis and a higher concentration of protein is contained in the urine of incident patients than the urine of normal healthy individuals.

The level of the protein content in the mouse urine was numerically expressed using Albustix (Ames urine protein test strips, produced by Siemens Healthcare K.K.) as urine protein test strips based on the following criteria.

negative: 0
±: 0.5
+: 1
2+: 2
3+: 3

Results

The results are illustrated in FIG. 7.

When Compound A was added (0.2 mg/kg and 1 mg/kg), a tendency of decrease in the protein content in the urine was found at any dose in 12 w or later compared with the control of adding no Compound A (saline in FIG. 7). In the 12th (1 mg/kg) and $18^{th}$ (0.2 mg/kg and 1 mg/kg) weeks, when Compound A was administered, significant (respectively, $p<0.05$) inhibitory effects on the protein content in the urine were found compared with the control (FIG. 7).

From these results, it was confirmed that Compound A exhibits excellent pharmacological action in vivo as well in prophylactic and therapeutic applications to nephritis due to inflammatory diseases, particularly autoimmune diseases.

Example 9 Inhibitory Effect on Tissue Lesion Using Inflammatory Disease Model Mice Developing Autoimmune Phenomena Materials and Method Present Example was performed simultaneously with Example 6 using MRL/lpr mice. Except for the following exceptions, present Example was performed by the same materials and method as Example 6 above.

After administration in the 16th week, 25-week-old mice were dissected and tissues (lacrimal glands, submandibular glands, and kidneys) were removed. After the removed tissues were rapidly frozen and embedded using O.C.T. compound (Sakura Finetek Japan Co., Ltd.), the frozen tissues were thin sectioned with a cryostat (LEICA CM 1920) and applied on glass slides. After the sections on the glass slides were dried, the tissues were stained by hematoxylin-eosin staining to be observed with a microscope. The hematoxylin-eosin staining was performed in the following procedure:

1) fixation and washing with an ethanol-formalin-acetic acid fixative;
2) adding New Hematoxylin solution Type G (Muto Pure Chemicals Co., Ltd.), followed by washing;
3) adding New Eosin solution Type A (Muto Pure Chemicals Co., Ltd.);
4) adding 80% ethanol;
5) adding xylene; and
6) mounted with Marinol (Muto Pure Chemicals Co., Ltd.) for observation.

Results

The results are illustrated respectively in FIGS. 8A (lacrimal glands), 8B (submandibular glands), and 8C (kidneys). In each illustration, the results of observing the stained tissue sections are illustrated in the case of, in order from the left, administering a physiological saline solution (not administering Compound A), administering 0.04 mg/kg Compound A, administering 0.2 mg/kg Compound A, and administering 1 mg/kg Compound A.

In the lacrimal gland tissues of the Compound A administered mice, the lymphocytic infiltration areas were clearly reduced compared with the lacrimal gland tissues of the control group mice (physiological saline solution administered mice) (FIG. 8A). Likewise, it became clear that, in the submandibular gland tissues (FIG. 8B) and the kidney tissues (FIG. 8C), the lymphocytic infiltration areas in the Compound A administered tissues were reduced compared with the tissues of the control group mice.

As the above results, reduction of lymphocytic infiltration in the lacrimal gland tissues, the submandibular gland tissues, and the kidney tissues were observed, and it was thus confirmed that Compound A is useful for prevention, inhibition of development, and/or improvement of inflammatory lesions of tissues frequently found in autoimmune diseases, such as Sjögren syndrome and systemic lupus erythematosus.

INDUSTRIAL APPLICABILITY

The prophylactic and/or therapeutic agent for inflammatory diseases containing the pyrrolopyrimidine compound, as an active ingredient, in the formula (1) of the present invention, such as Compound A of the present invention, can be used for prophylactic and therapeutic purposes against inflammatory diseases and autoimmune diseases, such as Sjögren syndrome and systemic lupus erythematosus, and thus is industrially applicable.

The invention claimed is:
1. A therapeutic agent for inflammatory disease, comprising: a compound or a salt thereof, or a solvate thereof, the compound represented by a formula (1) below:

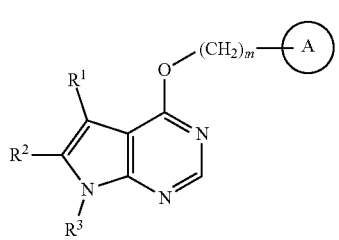
(1)

where a ring A denotes a group represented by a formula (A) below:

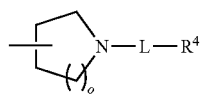
(A)

where $R^4$ denotes a ($C_{3-6}$ cycloalkyl) ($C_{1-3}$ alkyl) amino or nitrile group, L denotes a formula —$(CH_2)_n$—, —$CH_2C(O)$—, or —$C(O)CH_2$—, n denotes an integer from 0 to 3, and o denotes a natural number from 1 to 3, $R^1$ and $R^2$ are same or different from each other, and denote a hydrogen atom or a $C_{1-6}$ alkyl group, $R^3$ denotes a $C_{3-6}$ cycloalkyl group, a $C_{6-10}$ aryl group optionally substituted by a halogen atom, or a ($C_{6-10}$ aryl) $C_{1-6}$ alkyl group, and m denotes an integer from 0 to 2.

2. The therapeutic agent for inflammatory disease according to claim 1, wherein, in the formula (1), $R^4$ denotes a ($C_{3-6}$ cycloalkyl) ($C_{1-3}$ alkyl) amino group, L denotes a formula —$CH_2C(O)$—, o denotes 2, and m is 0.

3. The therapeutic agent for inflammatory disease according to claim 1, wherein, in the formula (1), $R^4$ denotes a cyclopropyl ($C_{1-3}$ alkyl) amino group.

4. The therapeutic agent for inflammatory disease according to claim 1, wherein the compound represented by the formula (1) is a compound represented by a formula (1') below:

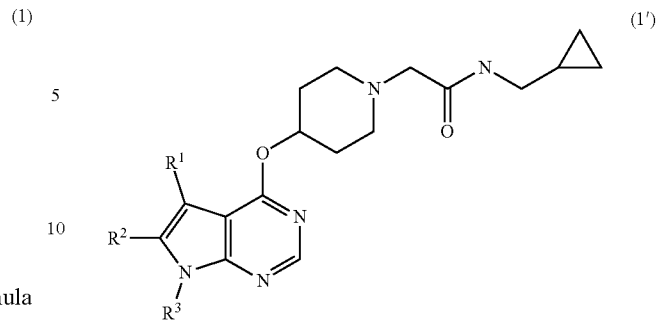
(1')

where $R^1$, $R^2$, and $R^3$ are same as respective definitions in the formula (1).

5. The therapeutic agent for inflammatory disease according to claim 1, wherein the compound in the formula (1) is 2-[4-{(7-benzyl-5,6-dimethyl-7H-pyrrolo[2,3-d]pyrimidin-4-yl)oxy}piperidin-1-yl]-N(cyclopropylmethyl)acetamide.

6. The therapeutic agent according to claim 1, wherein the inflammatory disease is an autoimmune disease.

7. The therapeutic agent according to claim 6, wherein the autoimmune disease is Sjögren syndrome or systemic lupus erythematosus.

8. The therapeutic agent according to claim 6, wherein the autoimmune disease is Sjögren syndrome.

9. The therapeutic agent according to claim 1, wherein the therapeutic agent is an oral agent.

10. The therapeutic agent according to claim 1, wherein the therapeutic agent is a parenteral agent.

11. The therapeutic agent according to claim 10, wherein the parenteral agent is an injection.

12. The therapeutic agent according to claim 10, wherein the parenteral agent is an ophthalmic preparation or a nasal preparation.

13. The therapeutic agent according to claim 10, wherein the parenteral agent is an ointment, a cream, a lotion, a gel preparation, or a spray.

* * * * *